(12) United States Patent
Gong et al.

(10) Patent No.: US 11,351,151 B2
(45) Date of Patent: Jun. 7, 2022

(54) COMPOUND HAVING ANTICANCER ACTIVITY AND PREPARATION METHOD AND APPLICATION

(71) Applicant: 3D Medicines (Beijing) Co., Ltd., Beijing (CN)

(72) Inventors: John Gong, Beijing (CN); Yihui Lin, Beijing (CN); Fengqing Li, Beijing (CN); Fangqiang Tang, Beijing (CN)

(73) Assignee: 3D MEDICINES (BEIJING) CO., LTD., Beijing (CN)

( * ) Notice: Subject to any disclaimer, the term of this patent is extended or adjusted under 35 U.S.C. 154(b) by 48 days.

(21) Appl. No.: 16/461,828

(22) PCT Filed: Nov. 17, 2017

(86) PCT No.: PCT/CN2017/111653
§ 371 (c)(1),
(2) Date: Oct. 23, 2019

(87) PCT Pub. No.: WO2018/090975
PCT Pub. Date: May 24, 2018

(65) Prior Publication Data
US 2020/0038371 A1     Feb. 6, 2020

(30) Foreign Application Priority Data

Nov. 17, 2016 (CN) .......................... 201611027194.X
May 10, 2017 (CN) .......................... 201710327784.2

(51) Int. Cl.
*A61K 31/416*     (2006.01)
*A61P 35/00*     (2006.01)

(52) U.S. Cl.
CPC ............ *A61K 31/416* (2013.01); *A61P 35/00* (2018.01)

(58) Field of Classification Search
CPC .... A61K 31/416; A61K 38/00; C07D 231/56; C07K 7/02
See application file for complete search history.

(56) References Cited

FOREIGN PATENT DOCUMENTS

| CN | 1826324 A | 8/2006 |
| CN | 101754955 A | 6/2010 |

OTHER PUBLICATIONS

B. Rodriguez-Spong et al. (Advanced Drug Delivery Reviews, 2004, 56, p. 263).*
Cancer defintion, MedicineNet.com—2005—p. 1.*
Stomach cancer—Mayoclinic.com—Apr. 9, 2011.*
GastricMALTLymphoma—LymphomaAssociation—2011.*
"Adult Brain Tumors Treatment", National Cancer Institute, pp. 1-21 (Jan. 24, 2013).*
"Types of Brain Cancer" at http://www.cancercenter.com/brain-cancer/types-of-brain-cancer.cfm (Mar. 12, 2013).*
"Colorectal Cancer" at cancer.net (published Sep. 2012), pp. 1-2.*
"Types of Breast Cancer", published in breastcancer.org (Sep. 30, 2012); p. 1.*
Cancer Drug Design and Discovery Neidle, Stephen, ed. (Elsevier/Academic Press, 2008) p. 428.*
Aversa et al. (Expert Review of Anticancer Therapy, vol. 15 (6), May 2015; p. 677-687—Abstract provided.*
International Search Report and Written Opinion dated Jan. 29, 2018 from the corresponding PCT Patent Application No. PCT/CN2017/111653.
Alan Ikeda et al; Research Article; Molecular Cancer Therapeutics; ABT-869 Inhibits the Proliferation of Ewing Sarcoma Cells and Suppresses Platelet-Derived Growth Factor Receptor β and c-KIT Signaling Pathways; published Online First Mar. 9, 2010; American Association for Cancer Research; 9 pages.
Jenny E. Hernandez-Davies et al; Therapeutic Discovery; The Multitargeted Receptor Tyrosine Kinase Inhibitor Linifanib (ABT-869) Induces Apoptosis through an Akt and Glycogen Synthase Kinase 3 β-Dependent Pathway; published Online First Apr. 6, 2011; American Association for Cancer Research; 12 pages.

(Continued)

*Primary Examiner* — Valerie Rodriguez-Garcia
(74) *Attorney, Agent, or Firm* — Grogan, Tuccillo & Vanderleeden LLP

(57) ABSTRACT

The present invention provides a compound exemplified by Formula I:

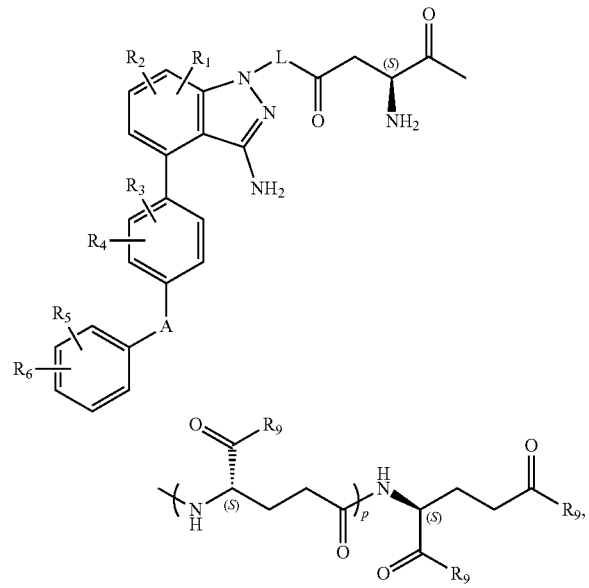

a process for its preparation and the use of a medicament for the treatment of cancer. The compound of the present invention has an inhibitory effect on various cancer cells and can be biologically converted into the active drug Linifanib in vitro (in liver homogenate and spleen homogenate) to inhibit the proliferation of tumor cells, especially liver cancer cells, at a lower dose.

9 Claims, 3 Drawing Sheets

(56) References Cited

OTHER PUBLICATIONS

Daniel H. Albert et al; Preclinical activity of ABT-869, a multitargeted receptor tyrosine kinase inhibitor; Cancer Research Global Pharmaceutical Research and Development, Abbott Laboratories, Mol Cancer Ther Apr. 2006, 13 pages.
Jun Guo, et al.; Inhibition of phosphorylation of the colony-stimulating factor-1 receptor (c-Fms) tyrosine kinase in transfected cells by ABT-869 and other tyrosine kinase inhibitors; Cancer Research Global Pharmaceutical Research and Development, Abbott Laboratories, Mol Cancer Ther Apr. 2006, 8 pages.
Hajime Asahina, et al.; An open-label, phase 1 study evaluating safety, tolerability, and pharmacokinetics of inifanib (ABT-869) in Japanese patients with solid tumors; Cancer Chemother Pharmacol (2012); 10 pages.
Yi-Lin Chiu; et al.; Results of a phse I, open-label, randomized, crossover study evaluating the effects of linifanib on TQc intervals in patients with solid tumors; Cancer Chemother Pharacol (2014); 5 pages.
Chiung-Ing Wong, et al.; Phase I and Biomarker Study of ABT-869, a Multiple Receptor Tyrosine Kinase Inhibitor, in Patients With Refractory Solid Malignancies; Journal of Clinical Oncology; vol. 27, No. 28, Oct. 2, 2009; 9 pages.
Deepa B. Shankar, et al.; ABT-869, a multitargeted receptor tyrosine kinase inhibitor: inhibition of FLT3 phosphorylation and signaling in acute myeloid leukemia; Prepublished online as Blood First Edition paper, Jan. 5, 2007; 9 pages.

\* cited by examiner

COMPOUND HAVING ANTICANCER ACTIVITY AND PREPARATION METHOD AND APPLICATION

CROSS REFERENCE TO RELATED APPLICATIONS

This application is a National Stage Patent Application of International Application No. PCT/CN2017/111653 filed on Nov. 17, 2017, which claims priority to Chinese Patent Application No. 201611027194.X filed on Dec. 27, 2017 and Chinese Patent Application No. 201710327784.2 filed on Dec. 27, 2017, which are incorporated by reference in their entireties.

TECHNICAL FIELD

The invention relates to a compound and a preparation method and application thereof, in particular, to a compound which can be selectively converted in vivo to have a stronger anticancer activity, and a preparation method and application thereof.

BACKGROUND

Using anti-tumor drugs to selectively kill tumor cells with less toxicity to normal cells has been a difficulty problem in tumor therapy. In recent years, the targeted therapy focusing on the mutation of specific targets in tumor cells has brought hope to cancer patients. However, targeted therapy also has many limitations such as a small population of beneficiary patients and rapid drug resistance after administration. New biomedical research and development taking a different approach to provide new treatment options for more patients is needed.

Linifanib is a multi-target anticancer compound which targets mostly angiogenesis-related kinase, and has good inhibitory effects on VEGFr, PDGFRs, CDF-1R and Flt-1/3. In a large randomized phase III clinical trial of liver cancer, Linifanib was found to be superior to the sole approved targeted drug Sorafenib in live cancer in parameters such as TTP (time to progression) and ORR (overall response rate) in liver cancer patients (TTP: 5.4 months vs. 4.0 months, ORR 13.0% vs. 6.9%). However, its toxicity and side effects are also greater than Sorafenib, thus, the overall efficacy is not stronger than Sorafenib, and therefore did not obtain FDA approval (J. Clin. Oncol., 2014, 33, 172-179).

DESCRIPTION OF INVENTION

In order to solve the above problems, the present application binds Linifanib or a derivative thereof to a polypeptide through a multi-carbon chain to form a compound Linifanib-Cx-AAy (i.e., a compound of formula I of the present invention); utilizing the high expression of PSMA (Prostate-Specific Membrane Antigen) in the tumor endothelial cells in solid tumors and in some tumor cells, specifically degrading Linifanib-Cx-AAy at the tumor site to form active anticancer compound Linifanib or its derivatives, therefore, the anti-cancer compound is specifically accumulated at the tumor site while reducing its systemic toxicity.

One aspect of the present application provides a compound having the structure of Formula I, a pharmaceutically acceptable salt, stereoisomer, solvate, or polymorph thereof:

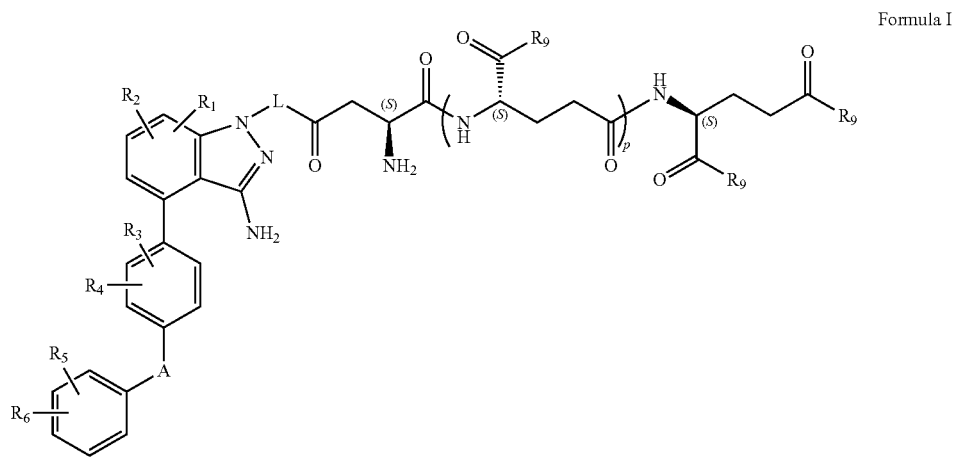

Formula I

Wherein,

A is selected from $(CH_2)eN(R_7)C(O)N(R_8)(CH_2)f$ and $CH_2C(O)NR_7$, wherein e and f are independently 0 or 1, wherein each group is bonded from its left to rings substituted by $R_3$ and $R_4$;

L is $-[Cm(O)(Z)n(NH)q]-$, where m, q are 0 or 1, n is 0-11, p is 0-8; Z is a group or several groups connected in the usual way from $-CR_{10}-$, $-CR_{10}-O-CR_{10}-$, $-S-S-$, $-CR_{10}=CR_{10}-$, $-CR_{10}\equiv CR_{10}-$, $-Ar$, $-CO-NH-$ and $-N=CR_{10}-$;

$R_1$ and $R_2$ are independently selected from the group consisting of hydrogen, alkoxy, alkoxyalkoxy, alkoxyalkyl, alkyl, aryloxy, aryloxyalkyl, halo, haloalkoxy, haloalkyl, heterocycle, heterocyclylalkenyl, heterocyclylalkoxy, heterocyclylalkyl, heterocyclyloxyalkyl, hydroxy, hydroxyalkoxy, hydroxyalkyl, (NRaRb)alkoxy, (NRaRb) Alkenyl, (NRaRb)alkyl, (NRaRb)carbonylalkenyl and (NRaRb)carbonylalkyl;

$R_3$ and $R_4$ are independently selected from the group consisting of hydrogen, alkoxy, alkyl, halo, haloalkoxy, haloalkyl and hydroxy;

$R_5$ and $R_6$ are independently selected from the group consisting of hydrogen, alkoxy, alkoxyalkyl, alkoxycarbonyl, alkyl, aryloxy, arylalkyl, carboxy, cyano, halo, haloalkoxy, haloalkyl, hydroxy, hydroxyalkyl, nitro and $-NRcRd$;

$R_7$ and $R_8$ are independently selected from the group consisting of hydrogen and alkyl;

$R_9$ is selected from the group consisting of hydrogen, hydroxy, amino, alkenyl, alkynyl, alkoxy, alkylamino, alkoxyalkyl, alkyl, alkoxycarbonyl, aryl, heterocycloalkyl;

$R_{10}$ is selected from the group consisting of hydrogen, alkyl, alkoxy, aryloxy, alkenyloxy, nitro, halo, primary, secondary and tertiary amine;

Ra and Rb are independently selected from the group consisting of hydrogen, alkyl, alkylcarbonyl, alkylsulfonyl, arylsulfonyl, haloalkylsulfonyl and heterocyclylsulfonyl;

Rc and Rd are independently selected from the group consisting of hydrogen, alkyl, alkylcarbonyl, aryl, arylalkyl, cycloalkyl, cycloalkylalkyl, heterocyclyl and heterocyclylalkyl.

Specifically, the structure of each compound is shown as follows:

| Number | Compound |
|---|---|
| 1 | |
| 2 | |
| 3 | |

| Number | Compound |
|---|---|
| 4 | 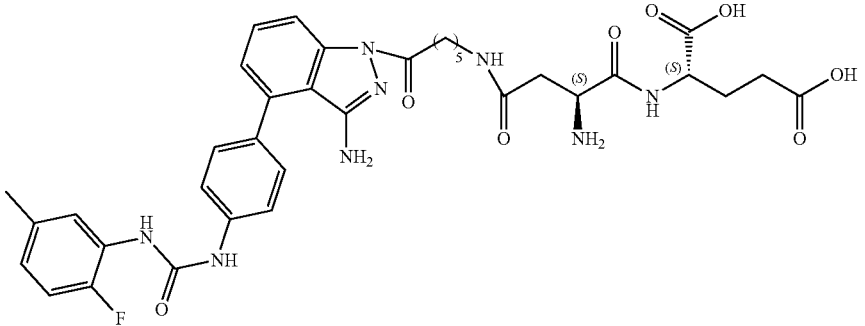 |
| 5 | 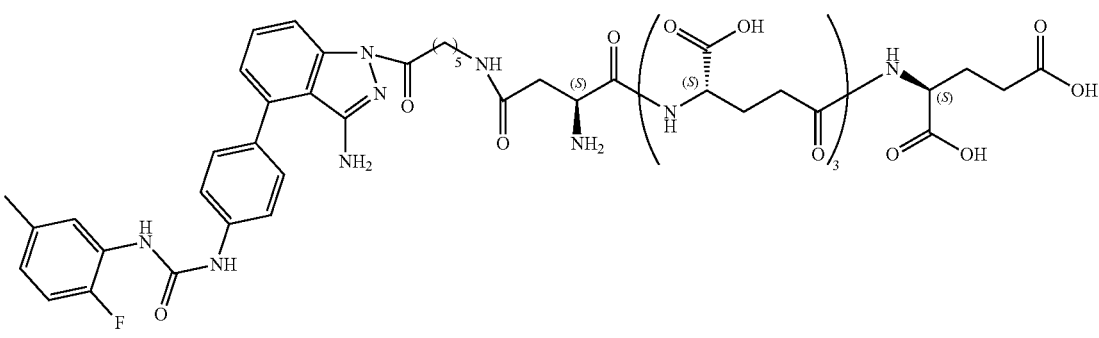 |
| 6 | 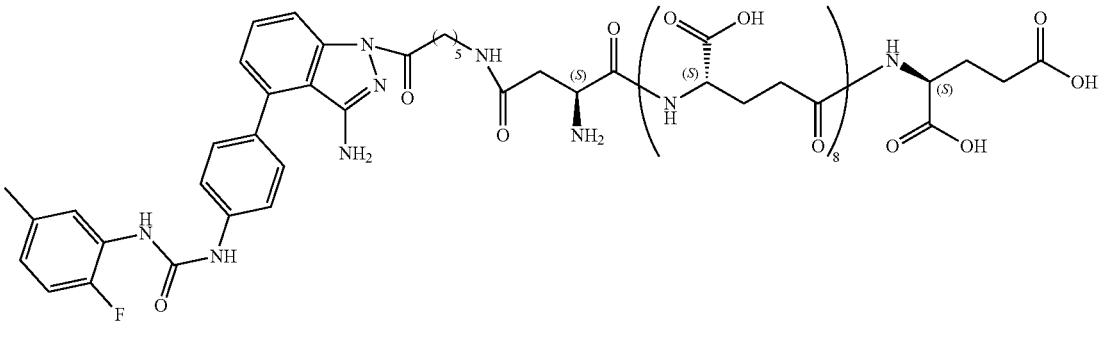 |
| 7 | 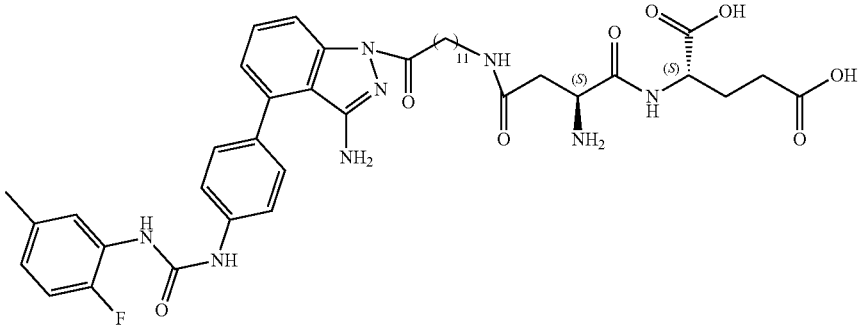 |

| Number | Compound |
|---|---|
| 8 (Lini-fanib-C12-AA5) | 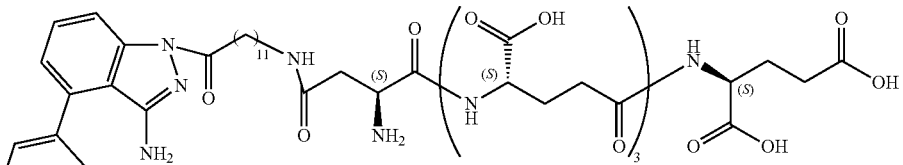 |
| 9 | 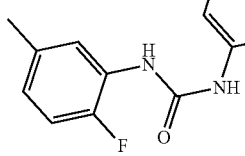 |

Reaction Route:

First, the polypeptide (reactant 1) and the benzyl-protected L (reactant 2) are reacted in the presence of a catalyst and a condensing agent to obtain a protected group-containing intermediate compound 1, which is further catalyze and hydrogenated in a polar solvent to remove the protecting group to obtain intermediate compound 2;

The intermediate compound 2 is reacted with Linifanib or a derivative thereof in the presence of a catalyst and a condensing agent to obtain a protecting group-containing intermediate compound 3, which further undergoes acidic conditions to remove the protecting group to obtain a compound of formula I.

Map of Reaction Route:

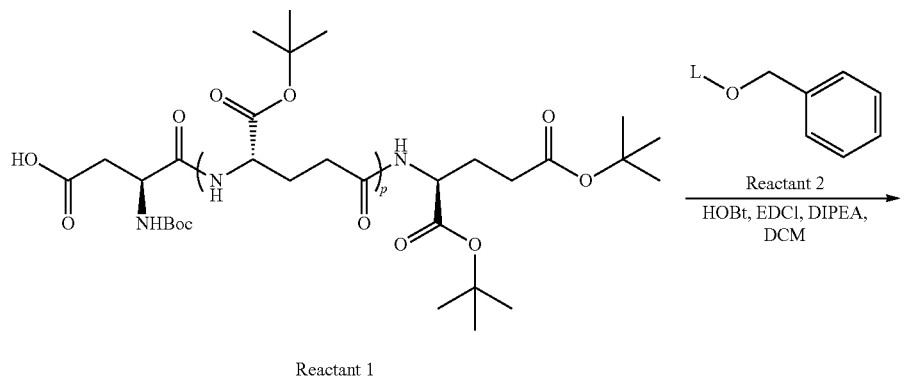

Reactant 1

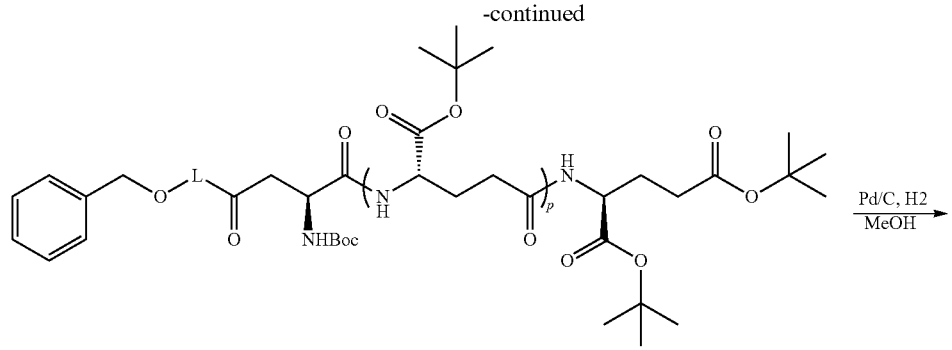
Intermediate compound 1
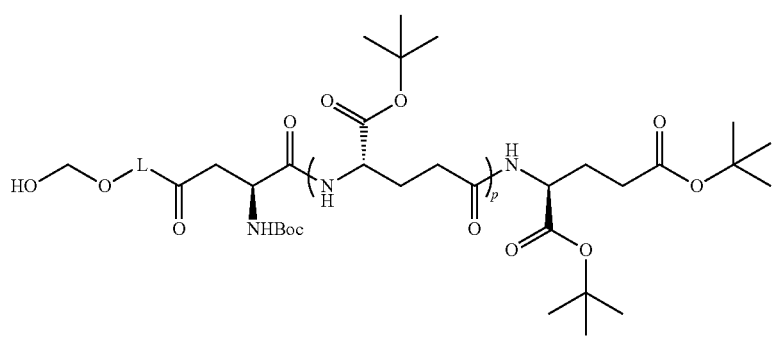
Intermediate compound 2
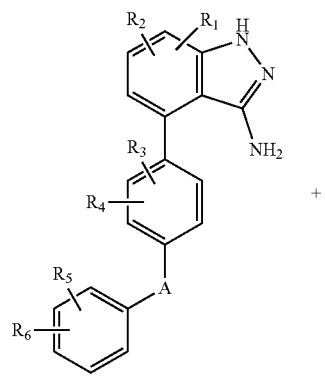
Linifanib or its derivatives
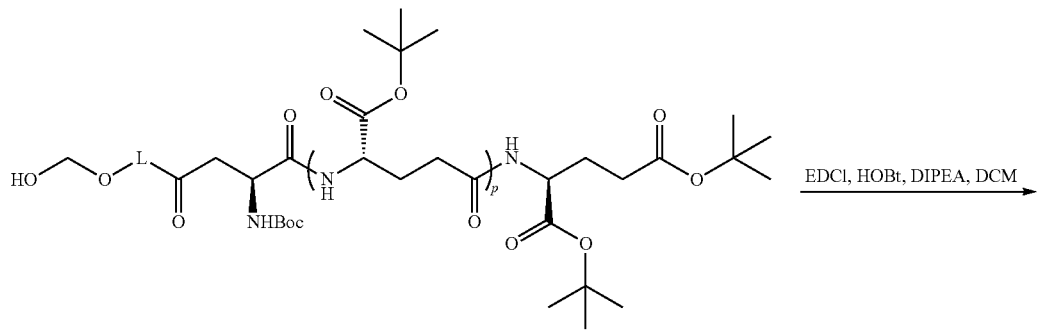
Intermediate compound 2

-continued

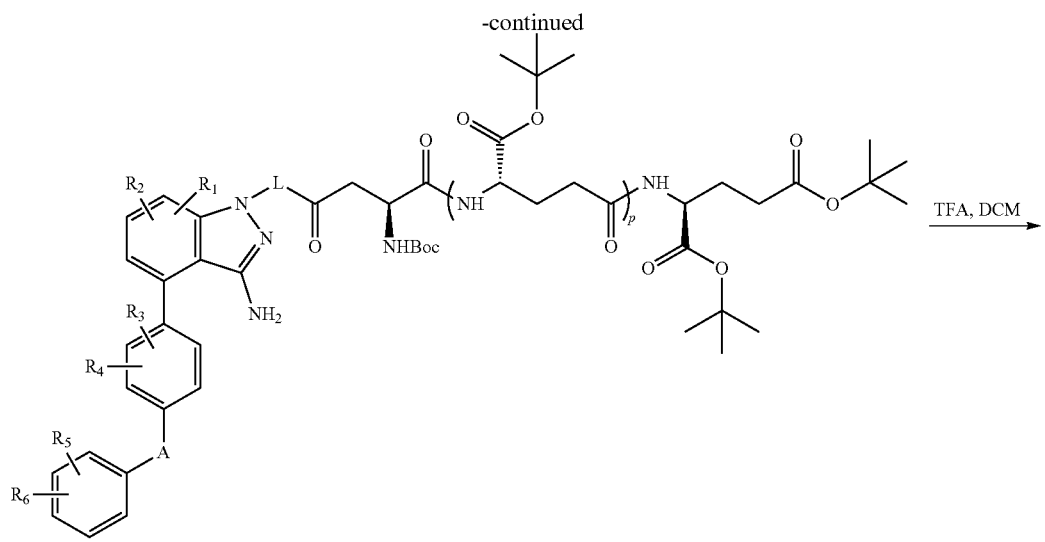

Intermediate compound 3

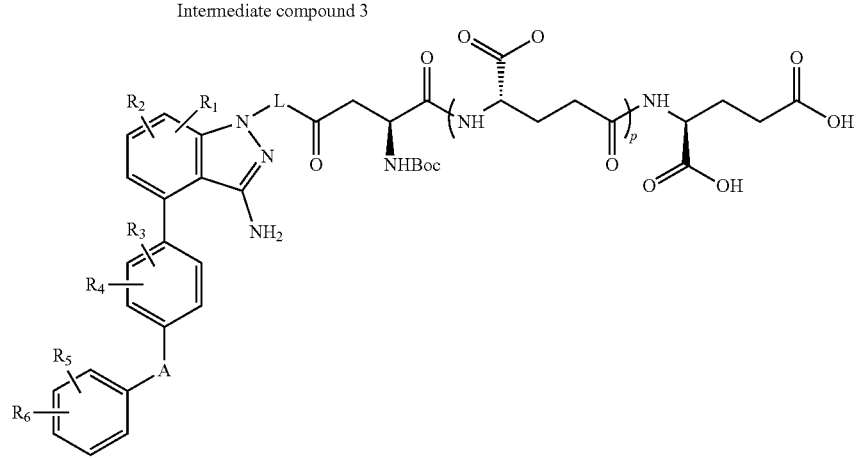

Compound of Formula I

Furthermore, in the above method for preparing the intermediate compound 1, the reaction temperature is carried out at −20° C. to 125° C.; the organic solvent is selected from the group consisting of ethers, alcohols, alkanes, aromatic hydrocarbons having 1 to 20 carbon atoms a ketone, an alkyl halide, an amide, a nitrile, an ester or a mixture thereof; the catalyst is 1-hydroxybenzotriazole (HOBT); the condensing agent is selected from any one or more from 1-ethyl-3-(3-dimethylaminopropyl), carbodiimide hydrochloride (MCI), 1,3-dicyclohexylcarbodiimide (DCC) or 4-dimethylaminopyridine (DMAP). In this step, the molar ratio of the reactants 1 and 2 in the reaction is 1:1 to 1:10, and the molar ratio of the reactant 1 to the condensing agent is 1:0.1 to 1:10; the molar ratio of the reactant 1 to the catalyst is 1:0.1 to 1:10.

Furthermore, in the above process for preparing the intermediate compound 2, the reaction temperature is carried out at −20° C. to 250° C.; the organic solvent is selected from the group consisting of ethers, alcohols, alkyl halides, amides, nitriles or mixtures thereof having from 1 to 20 carbon atoms, or a mixture with water in various ratios; the catalyst is palladium carbon, palladium hydroxide of dry or wet form. In the above preparation method, the molar ratio of the intermediate compound 2 to the catalyst is from 1:0.1 to 1:10.

Furthermore, in the above method for preparing the intermediate compound 3, the above reaction temperature is carried out at −20° C. to 125° C.; the organic solvent is selected from the group consisting of ethers, alcohols, alkanes, aromatic hydrocarbons, ketones, alkyl halides, amides, nitriles, esters, or a mixture thereof having from 1 to 20 carbon atoms; the catalyst is 1-hydroxybenzotriazole (HOBT); the condensing agent is any one or more of 1-ethyl-3-(3-dimethylaminopropyl) carbon diimine hydrochloride (EDCl), 1,3-dicyclohexylcarbodiimide (DCC) or 4-dimethylaminopyridine (DMAP). In this step, the molar ratio of Linifanib or its derivative to intermediate compound 2 is 1:1 to 1:10, the molar ratio of Linifanib or its derivative to condensing agent is 1:0.1 to 1:10, and the molar ratio to catalyst is 1:0.1 to 1:10.

Furthermore, in the above method for preparing the compound of the formula 1, the reaction temperature is carried out at −20° C. to 125° C.; the organic solvent is an ether, an alcohol, an alkane, an aromatic hydrocarbon, a ketone, a halogenated alkane, an amide, a nitrile, an ester or a mixture thereof in various ratios having from 1 to 20 carbon atoms; the acidic reagent is formic acid, acetic acid, trifluoroacetic acid. In the above preparation method, the molar ratio of the intermediate compound 3 to the acidic reagent is 1:1 to 1:10.

Another aspect of the present application provides a pharmaceutical composition comprising a compound of the above formula I, or a pharmaceutically acceptable salt, stereoisomer, solvate, polymorph thereof, and a pharmaceutically acceptable carrier according to the present application. The pharmaceutical compositions include, but are not limited to, oral dosage forms, parenteral dosage forms, topical dosage forms, and rectal administration dosage forms. In some examples, the pharmaceutical composition may be an oral tablet, capsule, pill, powder, sustained release preparation, solution and suspension; sterile solution, suspension or emulsion for parenteral injection; an ointment or cream for topical use; or a suppository for rectal administration. In some examples, the pharmaceutical composition and the at least one therapeutic agent are each combined in a separate dosage form into a combined product, such as a kit.

Another aspect of the present application provides a medicament prepared from an active ingredient and a pharmaceutically acceptable carrier, wherein the active ingredient is a compound of formula I or a pharmaceutically acceptable salt thereof, stereo Isomers, solvates, polymorphs, and pharmaceutically acceptable carriers. Such drugs include, but are not limited to, oral dosage forms, parenteral dosage forms, topical dosage forms, and rectal administration dosage forms. In some examples, the medicament may be an oral tablet, a capsule, a pill, a powder, a sustained release preparation, a solution and a suspension; a sterile solution, suspension or emulsion for parenteral injection; a topical ointment or cream; or a suppository for rectal administration. In some examples, the drug and the at least one therapeutic agent are each combined in a separate dosage form into a combined product, such as a kit.

Another aspect of the present application provides the use of a compound of formula I, a pharmaceutically acceptable salt, stereoisomer, solvate, polymorph thereof, for the manufacture of a medicament having anticancer effects. The cancer includes esophageal cancer, endometrial cancer, malignant lymphoma, multiple myeloma, gastrointestinal stromal tumor, colon cancer, rectal cancer, breast cancer, liver cancer, stomach cancer, ovarian cancer, uterine cancer, cervical cancer, Vaginal cancer, lung cancer, kidney cancer, prostate cancer, bladder cancer, pancreatic cancer, brain cancer, melanoma, etc. Preferably, the effect is optimal for liver cancer.

Another aspect of the present application provides a method of treating cancer comprising administering a therapeutically effective amount of a compound of formula I, a pharmaceutically acceptable salt, stereoisomer, solvate, polymorph thereof to individuals with the need. In some examples, the cancer comprises esophageal cancer, endometrial cancer, malignant lymphoma, multiple myeloma, gastrointestinal stromal tumor, colon cancer, rectal cancer, breast cancer, liver cancer, gastric cancer, ovarian cancer, Uterine cancer, cervical cancer, vaginal cancer, lung cancer, kidney cancer, prostate cancer, bladder cancer, pancreatic cancer, brain cancer, melanoma, etc. Preferably, the effect is optimal for liver cancer.

As used herein, "pharmaceutically acceptable salt" refers to a salt that retains the biological effectiveness of the free acid and free base of the specified compound, and which has no adverse effects biologically or otherwise. The salt in the present application means an acid salt formed with an organic acid/inorganic acid, and a basic salt formed with an organic base/inorganic base.

As used herein, "solvate" refers to a combination of a compound of the present application and a solvent molecule formed by solvation. Such as hydrates, ethanol solvates, methanol solvates, and the like.

As used herein, "polymorphs" or "polymorph" refers to a compound of the present application that exists in a different lattice form.

As used herein, "stereoisomer" refers to isomers resulting from the different arrangement of atoms in a molecule in space.

As used herein, "pharmaceutical composition" refers to a biologically active compound optionally mixed with at least one pharmaceutically acceptable chemical component including, but not limited to, carriers, stabilizers, diluents, dispersing agents, suspending agents, thickening agents and/or excipients. The "carrier" refers to a relatively non-toxic chemical agent that facilitates the introduction of a compound into a cell or tissue. As used herein, "alkyl" refers to a straight or branched saturated hydrocarbon chain containing from 1 to 10 carbon atoms, including but not limited to methyl, ethyl, n-propyl, isopropyl, n-butyl, Sec-butyl, isobutyl, tert-butyl, n-pentyl, isopentyl, neopentyl, n-hexyl, 3-methylhexyl, 2,2-dimethyl pentyl, 2,3-dimethyl Amyl, n-heptyl, n-octyl, n-decyl and n-decyl.

The "aryl group" means an aromatic carbocyclic group having 6 to 14 carbon ring atoms. The aryl group can be monocyclic or polycyclic. In the case of a polycyclic aromatic ring, only one of the polycyclic systems needs to be unsaturated, while the remaining one or more rings may be saturated, partially saturated or unsaturated. Examples of the aryl group include a phenyl group, a naphthyl group, an anthracenyl group, an indanyl group, and a tetrahydronaphthyl group.

The "heteroaryl" refers to a five- or six-membered aromatic ring having at least one carbon atom and one or more independently selected nitrogen, oxygen or sulfur atoms. Specifically, the "heteroaryl group" means an aromatic heterocyclic group having 5 to 14 ring atoms. The heteroaryl group can be a single ring or two or three fused rings. Examples of heteroaryl substituents include: 6-membered ring substituents such as pyridyl, pyrazinyl, pyrimidinyl, pyridazinyl and 1,3,5-, 1,2,4- or 1,2,3-triazinyl; 5-membered ring substituent such as imidazolyl, furyl, thienyl, pyrazolyl, oxazolyl, isoxazolyl, thiazolyl, 1,2,3-, 1,2,4-, 1,2,5-, or 1,3,4-oxadiazolyl and isothiazolyl; 6/5-membered fused ring substituents such as benzothienyl, benzisoxazolyl, benzoxazole Base, imidazolyl, fluorenyl, benzimidazolyl, pyrrolo[2,3-b]pyridinyl, fluorenyl; and 6/6-membered fused ring, such as benzopyranyl, quinolyl, isoquinolinyl, porphyrinyl, quinazolinyl and benzoxazinyl.

The "cycloalkenyl" refers to a monocyclic or bridged hydrocarbon ring system. The monocyclic cycloalkenyl group has 4, 5, 6, 7 or 8 carbon atoms and 0 heteroatoms. The four-membered ring system has one double bond, and the five- or six-membered ring system has one or two double bonds, and the seven- or eight-membered ring system has one, two or three double bonds. Representative examples of monocyclic cycloalkenyl include, but are not limited to, cyclobutenyl, cyclopentenyl, cyclohexenyl, cycloheptenyl, and cyclooctenyl.

The "heterocycloalkyl group" means a saturated ring structure containing a total of 3 to 14 ring atoms. At least one of the ring atoms is a hetero atom (i.e., oxygen, nitrogen or sulfur), and the remaining ring atoms are independently selected from the group consisting of carbon, oxygen, nitrogen and sulfur, such as tetrahydrofuranyl, tetrahydropyranyl, tetrahydrothiophenyl, pyrrolyl, pyrrolinyl, pyrrolidinyl, imidazolyl, imidazolinyl, imidazolidinyl, pyrazolyl, pyrazolinyl, pyrazolidinyl, triazolyl, tetrazolyl.

The term "effective amount" is meant a non-toxic, but sufficient amount of a drug or agent that provides the desired effect. In the pharmaceutical compositions or kits of the invention, an "effective amount" of an ingredient or formulation unit refers to an amount of the ingredient that is effective to provide the desired effect when used in combination with other ingredients. The "effective amount" will vary from subject to subject, depending on the age and general condition of the individual, the specific active drug, and the like. Thus, it is not always possible to refer to an accurate "effective amount", however, a suitable "effective amount" in any individual case can be determined by one of ordinary skill in the art using routine experimental methods.

The term "subject" can refer to a patient or other animal, particularly a mammal, such as a human, a dog, a monkey, a cow, a horse, etc., that receives a compound or pharmaceutical composition of the invention to treat, prevent, ameliorate, and/or alleviate the disease of the invention.

For in vitro experiments, the present application also synthesizes a metabolite of a compound of Formula I, a compound of Formula II, in the reaction route is as follows:

First, Linifanib or its derivative is reacted with Boc-protected L (Reactant 3) under the conditions of a condensing agent and a catalyst to form an intermediate compound Ma, which is under the action of trifluoroacetic acid to remove Boc protection to obtain Intermediate compound Mb; the intermediate compound Mb is further condensed with a protecting group of aspartic acid to obtain an intermediate compound Mc, and the intermediate compound Mc is under the trifluoroacetic acid condition to remove the Boc protection to form an intermediate compound Md, intermediate compound Md is catalyzed and hydrogenated under a noble metal catalyst condition to remove the benzyl group to obtain the metabolite of the compound of formula 2.

Map of Reaction Route:

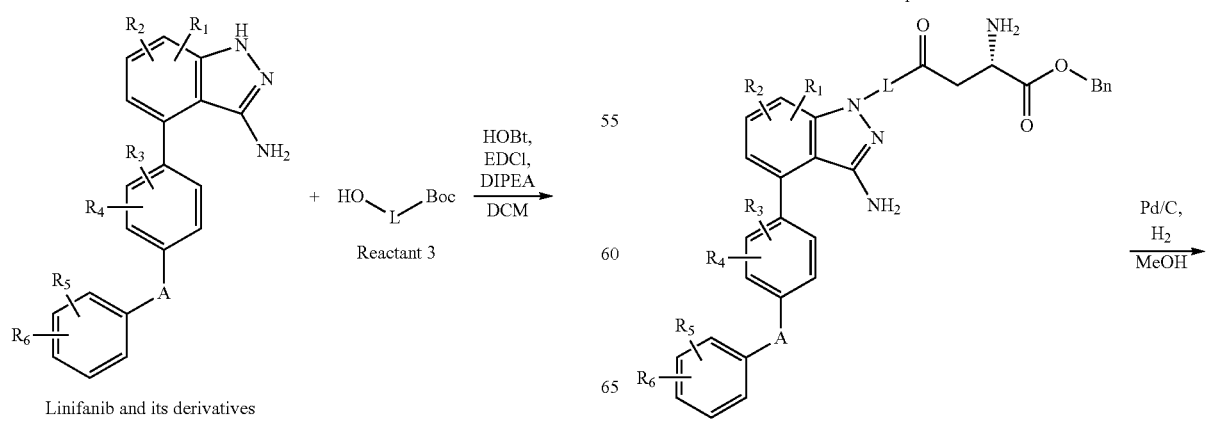

17
-continued

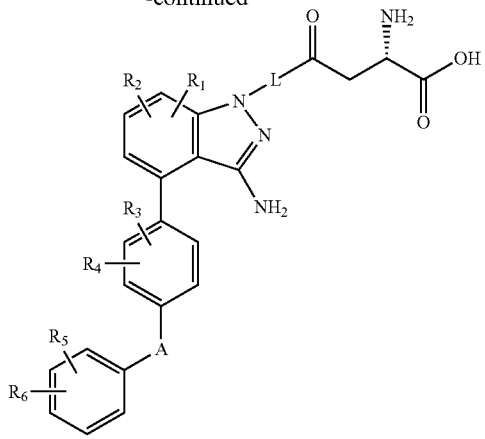

wherein,

A is selected from (CH$_2$)eN(R$_7$)C(O)N(R$_8$)(CH$_2$)f and CH$_2$C(O)NR$_7$, wherein e and f are independently 0 or 1, wherein each group is bonded from its left to rings substituted by R$_3$ and R$_4$;

L is —[Cm(O)(Z)n(NH)q]-, where m, q are 0 or 1, n is 0-11, p is 0-8; Z is one or several groups connected in the normal way selected from —CR$_{10}$—, —CR$_{10}$—O—CR$_{10}$—, —S—S—, —CR$_{10}$=CR$_{10}$—, —CR$_{10}$≡CR$_{10}$—, —Ar, —CO—NH— and —N=CR$_{10}$—;

R$_1$ and R$_2$ are independently selected from the group consisting of hydrogen, alkoxy, alkoxyalkoxy, alkoxyalkyl,

18 alkyl, aryloxy, aryloxyalkyl, halo, haloalkoxy, haloalkyl, heterocycle, heterocyclylalkenyl, heterocyclylalkoxy, heterocyclylalkyl, heterocyclyloxyalkyl, hydroxy, hydroxyalkoxy, hydroxyalkyl, (NRaRb)alkoxy, (NRaRb) Alkenyl, (NRaRb)alkyl, (NRaRb)carbonylalkenyl and (NRaRb)carbonylalkyl;

R$_3$ and R$_4$ are independently selected from the group consisting of hydrogen, alkoxy, alkyl, halo, haloalkoxy, haloalkyl and hydroxy;

R$_5$ and R$_6$ are independently selected from the group consisting of hydrogen, alkoxy, alkoxyalkyl, alkoxycarbonyl, alkyl, aryloxy, arylalkyl, carboxy, cyano, halo, haloalkoxy, haloalkyl, Hydroxy, hydroxyalkyl, nitro and —NRcRd;

R$_7$ and R$_8$ are independently selected from the group consisting of hydrogen and alkyl;

R10 is selected from the group consisting of hydrogen, alkyl, alkoxy, aryloxy, alkenyloxy, nitro, halo, primary, secondary and tertiary amine;

Ra and Rb are independently selected from the group consisting of hydrogen, alkyl, alkylcarbonyl, alkylsulfonyl, arylsulfonyl, haloalkylsulfonyl and heterocyclylsulfonyl;

Rc and Rd are independently selected from the group consisting of hydrogen, alkyl, alkylcarbonyl, aryl, arylalkyl, cycloalkyl, cycloalkylalkyl, heterocyclyl and heterocyclylalkyl.

Specifically, the structure of each metabolite is shown as follows:

| Number | Compound |
|--------|----------|
| 10 | 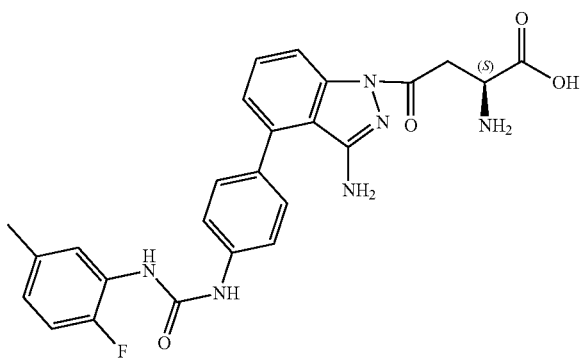 |
| 11 | 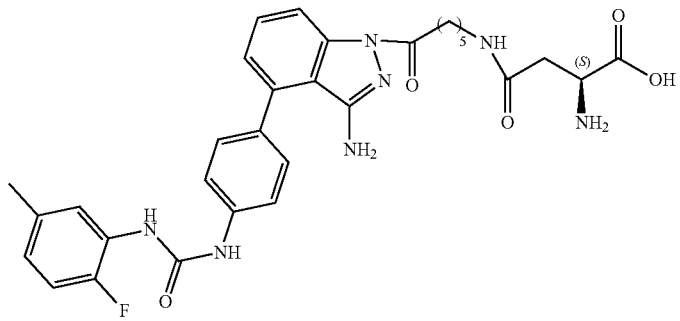 |

| Number | Compound |
|---|---|
| 12 Linifanib-C12-Asp | 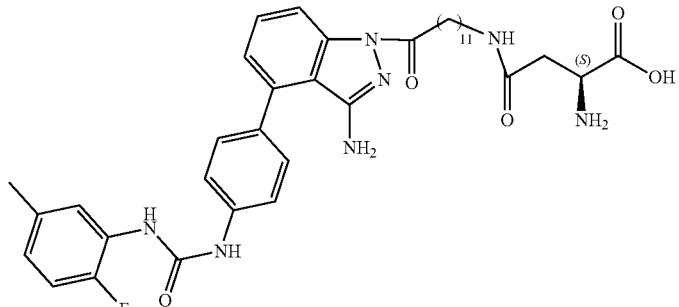 |

In the synthesis stage of the present invention, attempts to structurally link carbon chains and amino acids at multiple sites of Linifanib have been made, but the results are not satisfactory, most of the compounds are not synthesized successfully, the yield is very low, and although some compounds are successfully synthesized, they do not act to block the activity of Linifanib, or they cannot be stably present in plasma. In the end, only one product of the ligation is not only high in yield, but also can successfully block the activity of Linifanib, and can be biologically converted into the active drug Linifanib in vitro (in liver homogenate and spleen homogenate) to inhibit tumor cells at a lower dose, especially inhibit the proliferation of liver cancer cells.

EXAMPLES

Figure 1:
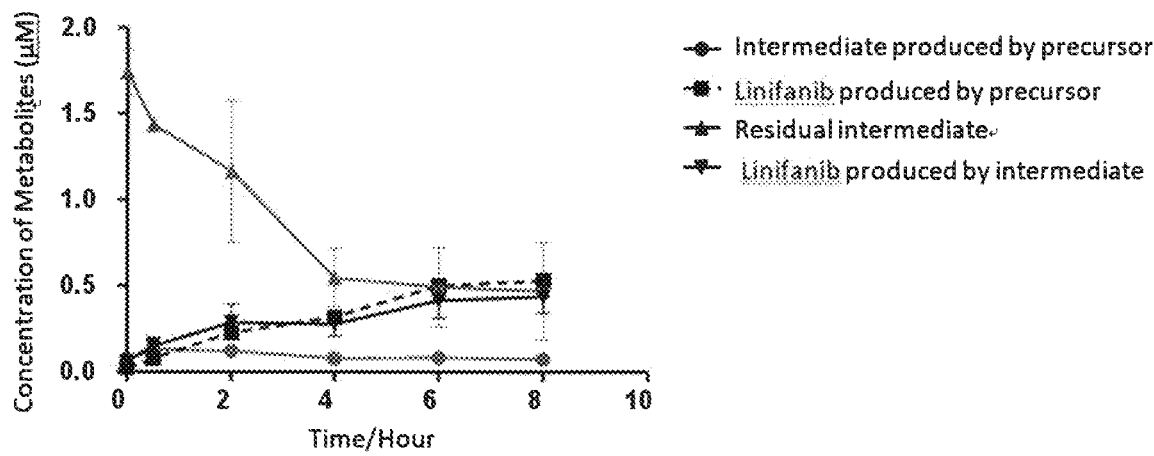
FIG. 1 shows the first experiment of the stability of the precursor and intermediate in liver homogenate

Examples 1 and 2: Preparation of Target Compound 1

Example 1 Preparation of Intermediate Compound 3

Weighed and took 600 mg of Linifanib (1.6 mmol), 324 mg of HOBT (2.4 mmol), and 460 mg of EDCl (2.4 mmol) to dissolve in 50 ml of dichloromethane, stirred and reacted for 0.5 h, controlling reaction temperature at 20~40° C. and slowly added 912 mg of the intermediates compound 2 Asp (BOC)-Glu (OtBu)-(OtBu) (1.92 mmol) which is available in market, and finally added 516 mg of DIPEA (4.0 mmol); maintaining the reaction temperature and stirring reacting for 12 h. TLC (DCM/MeOH=40:1) detected a complete reaction. 100 ml of dichloromethane was added to dilute the reaction solution, and the solution was washed with 250 ml deionized water twice. The organic phase was then washed with 150 ml saturated sodium solution, and the organic phase was dried with anhydrous sodium sulfate. Desiccant was filtered and concentrated at low temperature to obtain a brown oily object. The oily object was carried out by Silica Gel column chromatography (DCM:MeOH=0:1~100:1), and 716 mg of a white solid powder was obtain, with a yield rate of 53.8%.

Example 2 Preparation of Target Compound 1

Weighed and took 500 mg of the intermediate Compound 3 (0.38 mmol) prepared in Example 1 to dissolve in 20 ml dichloromethane, the reaction temperature was controlled at −5~5° C. Slowly added 3 ml of trifluoroacetate (0.04 mmol), and the reaction temperature was maintained and stir-reacted for 20~24 h; TLC (DCM/MeOH=40:1) detected a complete reaction. Added 40 ml of dichloromethane to dilute to the reaction solution, washed two times with 120 ml of deionized water, then wash two times with 60 ml of 5% sodium bicarbonate solution, and then washed two times with 120 ml of deionized water. Organic phase was separated and dried with anhydrous sodium sulfate. Desiccant was filtered and concentrated at low temperature to obtain a reddish-brown oily object. The oily object was prepared by chromatographic separation, and 106 mg of a white solid powder was obtained with a yield rate of 44.9%. $^1$HNMR (400 MHz, DMSO-d6) Delta: 9.37 (S, 1H), 8.67 (S, 1H), 8.32-8.27 (M, 2H), 7.99-7.96 (M, 1H), 7.65-7.59 (M, 3H), 7.42-7.39 (M, 2H), 7.27-7.18 (M, 2H), 7.13-7.08 (M, 1H), 6.81-6.78 (M, 2H), 5.25 (S, 2H), 4.34-4.11 (M, 2H), 3.71-3.60 (M, 1H), 2.91-2.81 (M, 1H), 2.37-2.31 (M, 2H), 2.28 (S, 3H), 2.24-2.20 (M, 1H), 1.89-1.86 (M, 1H). HPLC purity: 96.1% (214 nm), 95.5% (254 nm). MS (ESI): m/z 620.0 [M+1]$^+$ Chemical Structure is:

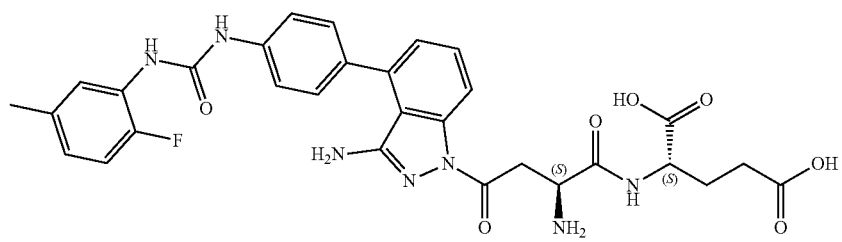

Examples 3-4: Preparation of Target Compound 2

Example 3 Preparation of Intermediate Compound 3

Weighed and took 600 mg of Linifanib (1.6 mmol), 324 mg of HOBT (2.4 mmol) and 460 mg of EDCl (2.4 mmol) to dissolve in 50 ml of dichloromethane and stir-reacted for 0.5 h, and controlled the reaction temperature at 20~40° C. slowly added 1978 mg of Intermediate compound 2 Asp(Boc)-Glu(OtBu)-Glu(OtBu)-Glu(OtBu)-Glu(OtBu)-(OtBu) (1.92 mmol) which is available in market, and finally added 516 mg of DIPEA (4.0 mmol). The reaction temperature was maintained and stir-reacted for 12 h, and TLC (DCM/MeOH=40:1) detected the completion of reaction. The reaction solution was diluted with 100 ml of dichloromethane, washed twice with 250 ml of deionized water, and the organic phase was separated. The organic phase was washed with 150 ml of saturated sodium solution and separated. The desiccant was filtered off and the filtrate was concentrated at low temperature to give a brown oily object. The oily object was subjected to silica gel column chromatography (DCM:MeOH=0:1 to 100:1) to give 1038 mg of white solid powder, and the yield rate was 46.8%.

Example 4 Preparation of Target Compound 2

The intermediate compound prepared in Example 3 was weighed and took 527 mg (0.38 mmol) to dissolve in 20 ml of dichloromethane, and the reaction temperature was controlled at −5 to 5° C., and 3 ml (0.04 mmol) of trifluoroacetic acid was slowly added to maintain the reaction temperature. The reaction was stirred for 20-24 h, and the reaction was complete by TLC (DCM/MeOH=40:1). The reaction solution was diluted with 40 ml of dichloromethane, washed twice with 120 ml of deionized water, twice with 60 ml of 5% sodium hydrogen carbonate solution, and twice with 120 ml of deionized water. The organic phase was separated, and the organic phase was dried over anhydrous sodium sulfate. The desiccant was filtered off and the filtrate was concentrated at low temperature to give a red brown oily object. The oily object was subjected to chromatography to give 166 mg of white solid powder, and the yield rate as 43.5%. HPLC purity: 95.9% (214 nm), 96.5% (254 nm). MS (ESI): m/z 1007.0 [M+1]$^+$ The chemical structure is:

Examples 5-6: Preparation of Target Compound 3

Example 5 Preparation of Intermediate Compound 3

Weighed 600 mg of Linifanib (1.6 mmol), 324 mg of HOBT (2.4 mmol) and 460 mg of EDCl (2.4 mmol) to dissolve in 50 ml of dichloromethane, stir-reacted for 0.5 h, and controlled the reaction temperature at 20~40° C. Slowly added 3,756 mg of intermediate compound 2 Asp(Boc)-Glu(OtBu)-Glu(OtBu)-Glu(OtBu)-Glu(OtBu)-Glu(OtBu)-Glu(OtBu)-Glu(OtBu)-Glu (OtBu)-(OtBu) (1.92 mmol) which is available in market, and finally DIPEA 516 mg (4.0 mmol) was added, and the reaction was stirred for 12 h, and the reaction was completed by TLC (DCM/MeOH=40:1). The reaction solution was diluted with 100 ml of dichloromethane, washed twice with 250 ml of deionized water, and the organic phase was separated. The organic phase was washed with 150 ml of saturated sodium solution and separated. The desiccant was filtered off and the filtrate was concentrated at low temperature to give a brown oily object. The oily object was subjected to silica gel column chromatography (DCM:MeOH=0:1 to 100:1) to give 1051 mg of white solid powder, with a yield rate of 28.4%.

Example 6 Preparation of Target Compound 3

879 mg of the intermediate compound 3 prepared in Example 5 was weighed (0.38 mmol) and dissolved in 20 ml of dichloromethane, and the reaction temperature was controlled at −5 to 5° C. 3 ml of trifluoroacetic acid (0.04 mmol) was slowly added to maintain the reaction temperature. The reaction was stirred for 20-24 h, and the reaction was completed by TLC (DCM/MeOH=40:1). The reaction solution was diluted with 40 ml of dichloromethane, washed twice with 120 ml of deionized water, twice with 60 ml of 5% sodium hydrogen carbonate solution, and twice with 120 ml of deionized water. The organic phase was separated, and the organic phase was dried over anhydrous sodium sulfate. The desiccant was filtered off and the filtrate was concentrated at low temperature to give a red brown oily object. The oily object was subjected to chromatography to give 174 mg of a white solid powder, the yield rate was 27.7%. HPLC purity: 92.5% (214 nm), 94.1% (254 nm). MS (ESI): m/z 1652.0 [M+1]$^+$

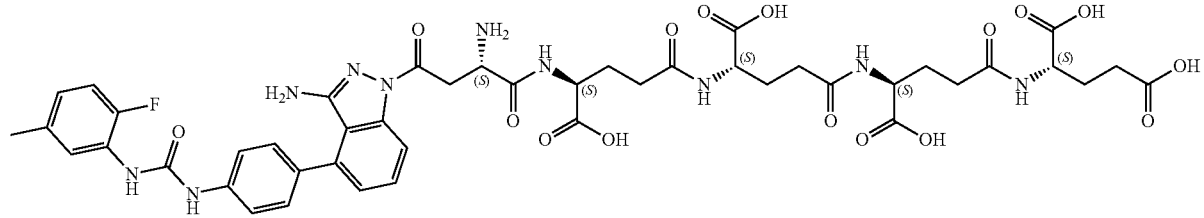

Chemical structure is:

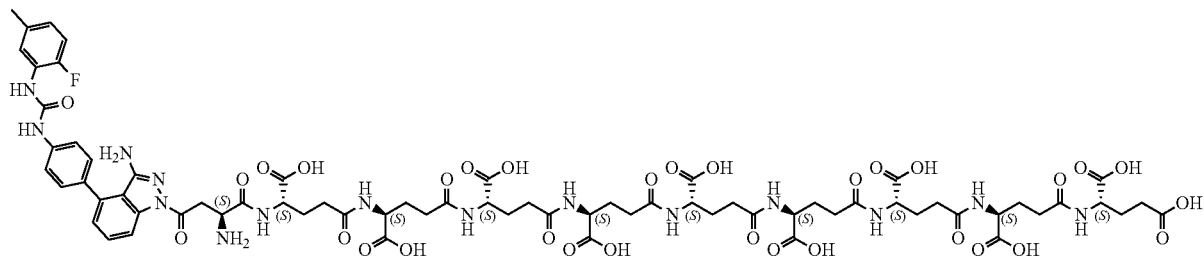

Examples 7-10: Preparation of Target Compound 4

Example 7 Preparation of Intermediate Compound 1

Weighed 304 mg of benzyl-(6-amino)hexaneate hydrochloride (1.18 mmol), 238 mg of HOBT (1.76 mmol) and 192 mg of MCI 192 (1.76 mmol) to dissolve in 50 ml of dichloromethane, stirred at room temperature. Controlled reaction temperature at 20~40° C. Slowly added 584 mg of Asp(Boc)-Glu(OtBu)-(OtBu) (1.23 mmol), maintained the reaction temperature, stir-reacted for 4 h, TLC (DCM/MeOH=40:1)) detected the completion of the reaction. The reaction solution was diluted with 100 ml of dichloromethane, washed twice with 250 ml of deionized water, and the organic phase was separated. The organic phase was washed with 150 ml of saturated sodium solution and separated. The desiccant was filtered off and the filtrate was concentrated at low temperature to give a brown oily object. The oily object was subjected to silica gel column chromatography (petroleum ether/acetone=10:1 to 2:1) to yield 338 mg of a yellow solid powder; the yield rate was 42.3%.

Example 8 Preparation of Intermediate Compound 2

Weighed 285 mg of the intermediate compound 1 (0.42 mmol) prepared in Example 7 and dissolved in 60 ml of anhydrous methanol, and 10% Pd/C 25 mg was added under nitrogen atmosphere, and hydrogen was introduced and exchanged three times. The reaction was controlled at 2 MPa in the atmosphere, and the reaction was carried out at 20-65° C. for 6-12 h. The reaction was complete by TLC (DCM/MeOH=40:1). The reaction solution was filtered under nitrogen atmosphere to recover palladium carbon. The filtrate was concentrated at low temperature to give a yellow brown oily object. The oily object was subjected to chromatography to give 115 mg of pale-yellow solid powder, and yield rate was 46.6%.

Example 9 Preparation of Intermediate Compound 3

Weighed 600 mg of Linifanib (1.6 mmol), 324 mg of HOBT (2.4 mmol) and 460 mg of EDCl (2.4 mmol) to dissolve in 50 ml of dichloromethane, stirred the reaction for 0.5 h, controlled the reaction temperature 20~40° C. Slowly added 1129 mg of intermediate compound 2 (1.92 mmol) prepared in example 8 and finally DIPEA 516 mg (4.0 mmol) was added, and the reaction was stirred for 12 h, and the reaction was completed by TLC (DCM/MeOH=40:1). The reaction solution was diluted with 100 ml of dichloromethane, washed twice with 250 ml of deionized water, and the organic phase was separated. The organic phase was washed with 150 ml of saturated sodium solution, separated and dried with anhydrous sodium sulfate. The desiccant was filtered off and the filtrate was concentrated at low temperature to give a brown oily object. The oily object was subjected to silica gel column chromatography (DCM:MeOH=0:1 to 100:1) to give 776 mg of a white powder, and the yield rate was 51.3%.

Example 10 Preparation of Target Compound 4

Weighed 595 mg of the intermediate compound 3 (0.63 mmol) prepared in Example 9 to dissolve in 20 ml of dichloromethane, controlled the reaction temperature at −5~5° C. Slowly added 3 ml (0.04 mmol) of trifluoroacetic acid, maintained the reaction temperature. The reaction was stirred for 20-24 h, and the reaction was completed by TLC (DCM/MeOH=40:1). The reaction solution was diluted with 40 ml of dichloromethane, washed twice with 120 ml of deionized water, twice with 60 ml of 5% sodium hydrogen carbonate solution, and twice with 120 ml of deionized water. The organic phase was separated, and the organic phase was dried with anhydrous sodium sulfate. The desiccant was filtered off and the filtrate was concentrated at low temperature to give a red brown oily object. The oily object was subjected to chromatography to give 193 mg of a white solid powder, yield rate was 41.9%. $^1$HNMR (400 MHz, DMSO-d6) δ: 9.30 (s, 1H), 8.67 (d, J=7.6 Hz, 1H), 8.58 (d, J=2.0 Hz, 1H) 8.31 (d, J=8.0 Hz, 1H) 8.25-8.22 (m, 1H), 8.09 (s, 3H), 7.99 (d, J=6.4 Hz, 1H), 7.64-7.58 (m, 3H), 7.41 (d, J=8.4 Hz, 1H), 7.19-7.09 (m, 2H), 6.83 (d, J=5.6 Hz, 1H), 5.17 (s, 2H), 4.26-4.14 (m, 2H), 3.15-2.97 (m, 4H), 2.70-2.54 (m, 2H), 2.33-2.32 (m, 2H), 2.28 (s, 3H), 2.00-1.69 (m, 4H), 1.50-1.36 (m, 4H). HPLC purity: 98.2% (214 nm), 98.5% (254 nm). MS (HI): m/z 733.0 [M+1]$^+$ The chemical structure is:

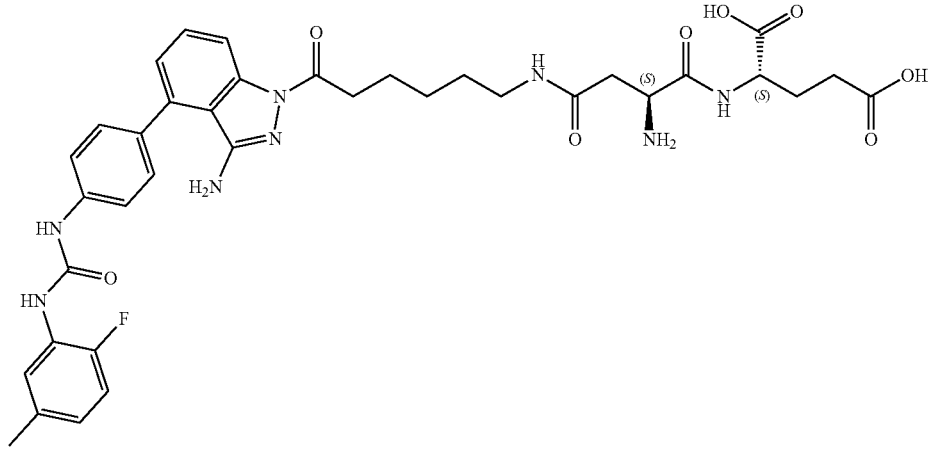

Examples 11-14: Preparation of Target Compound 5

Example 11 Preparation of Intermediate Compound 1

Weighed 304 mg of benzyl-(6-amino)hexaneate hydrochloride (1.18 mmol), 238 mg of HOBT (1.76 mmol) and 192 mg of MCI (1.76 mmol) to dissolve in 50 ml of dichloromethane, stirred at room temperature. Controlled reaction temperature at 20~40° C. Slowly added 1267 mg of Asp(Boc)-Glu(OtBu)-Glu(OtBu)-Glu(OtBu)-Glu(OtBu)-(OtBu) (1.23 mmol), and maintained the reaction temperature and stir-reacted for 4 h, and the reaction was completed by TLC (DCM/MeOH=40:1). The reaction solution was diluted with 100 ml of dichloromethane, washed twice with 250 ml of deionized water, and the organic phase was separated. The organic phase was washed with 150 ml of saturated sodium solution and separated. The organic phase was dried with anhydrous sodium sulfate. The desiccant was filtered off and the filtrate was concentrated at low temperature to give a brown oily object. The oil was subjected to silica gel column chromatography (peel ether/acetone=10:1 to 2:1) to yield 544 mg of a yellow solid powder. The yield rate was 37.4%.

Example 12 Preparation of Intermediate Compound 2

518 mg of the intermediate compound 1 (0.42 mmol) prepared in Example 11 was weighed and dissolved in 60 ml of anhydrous methanol, and 10% Pd/C 25 mg was added under nitrogen atmosphere, and hydrogen was introduced and exchanged for 3 times. The reaction was controlled at 2 MPa in the atmosphere, and the reaction was carried out at 20-65° C. for 6-12 h. The reaction was completed by TLC (DCM/MeOH=40:1). The reaction solution was filtered under nitrogen atmosphere to recover palladium carbon. The filtrate was concentrated at low temperature to give a yellow-brown oily object. The oily object was subjected to chromatography to give 244 mg of a pale-yellow solid powder, yield rate was 50.8%.

Example 13 Preparation of Intermediate Compound 3

Weighed 600 mg of Linifanib 600 (1.6 mmol), 324 mg of HOBT (2.4 mmol) and 460 mg of EDCl (2.4 mmol) to dissolve in 50 ml of dichloromethane, stirred the reaction for 0.5 h, controlled the reaction temperature at 20~40° C. Slowly added 2195 mg of the intermediate compound 2 (1.92 mmol) prepared in example 12, and finally DIPEA 516 mg (4.0 mmol) was added, the reaction was stirred for 12 h, and the reaction was completed by TLC (DCM/MeOH=40:1). The reaction solution was diluted with 100 ml of dichloromethane, washed twice with 250 ml of deionized water, and the organic phase was separated. The organic phase was washed with 150 ml of saturated sodium solution, separated and dried with anhydrous sodium sulfate. The desiccant was filtered off and the filtrate was concentrated at low temperature to give a brown oily object. The oily object was subjected to silica gel column chromatography (DCM:MeOH=0:1 to 100:1) to yield 1054 mg of a white solid powder, the yield rate was 43.9%.

Example 14 Preparation of Target Compound 5

Weighed 945 mg of the intermediate compound 3 (0.63 mmol) prepared in Example 13 and dissolve it in 20 ml of dichloromethane. Controlled the reaction temperature at −5~5° C. Slowly added 3 ml (0.04 mmol) of trifluoroacetic acid to maintain the reaction temperature. The reaction was stirred for 20-24 h, and the reaction was completed by TLC (DCM/MeOH=40:1). The reaction solution was diluted with 40 ml of dichloromethane, washed twice with 120 ml of deionized water, twice with 60 ml of 5% sodium hydrogen carbonate solution, and twice with 120 ml of deionized water. The organic phase was separated, and the organic phase was dried with anhydrous sodium sulfate. The desiccant was filtered off and the filtrate was concentrated at low temperature to give a red brown oily object. The oily object was subjected to chromatography to give 273 mg of a white solid powder, yield rate was 38.7%. HPLC purity: 97.2% (214 nm), 98.4% (254 nm). MS (ESI): m/z 1120.0 [M+1]$^+$ The chemical structure is:

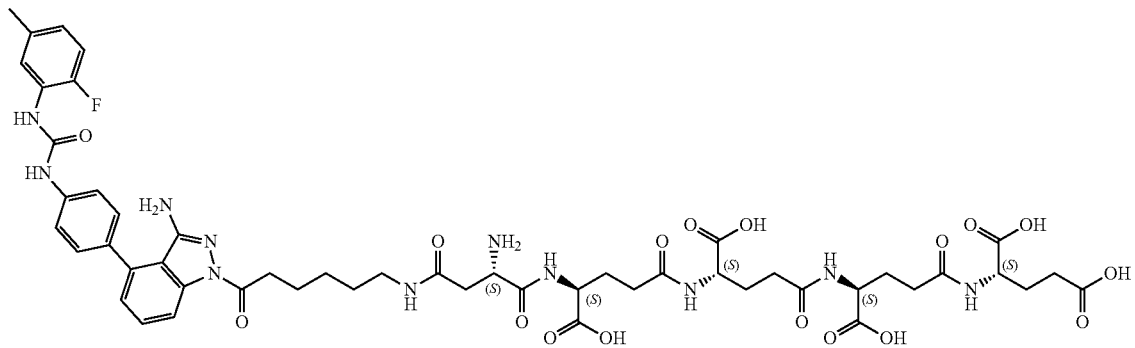

Examples 15-18: Preparation of Target Compound 6

Example 15 Preparation of Intermediate Compound 1

Weighed 304 mg of benzyl-(6-amino)hexaneate hydrochloride (1.18 mmol), 238 mg of HOBT (1.76 mmol), 192 mg of MCI (1.76 mmol) to dissolve in 50 ml of dichloromethane, stirred at room temperature. Controlled reaction temperature at 20~40° C. Slowly added 2406 mg of Asp(Boc)-Glu(OtBu)-Glu(OtBu)-Glu(OtBu)-Glu(OtBu)-Glu(OtBu)-Glu(OtBu)-Glu(OtBu)-Glu (OtBu)-Glu(OtBu)-(OtBu) (1.23 mmol), maintained the reaction temperature and the reaction was stirred for 4 h, and the reaction was completed by TLC (DCM/MeOH=40:1). The reaction solution was diluted with 100 ml of dichloromethane, washed twice with 250 ml of deionized water, and the organic phase was separated. The organic phase was washed with 150 ml saturated sodium solution and separated. The desiccant was filtered off and the filtrate was concentrated at low temperature to give a brown oily object. The oily object was subjected to silica gel column chromatography (petrol ether/acetone=10:1 to 2:1) to give 724 mg of a yellow solid powder, the yield rate was 28.4%.

Example 16 Preparation of Intermediate Compound 2

907 mg of the intermediate compound 1 (0.42 mmol) prepared in Example 15 was weighed and dissolved in 60 ml of anhydrous methanol, and 10% Pd/C 25 mg was added under nitrogen atmosphere, and hydrogen was introduced and exchanged three times. The reaction was controlled at 2 MPa in the atmosphere, and the reaction was carried out at 20-65° C. for 6-12 h. The reaction was completed by TLC (DCM/MeOH=40:1). The reaction solution was filtered under nitrogen atmosphere to recover palladium carbon. The filtrate was concentrated at low temperature to give a yellow brown oily object. The oily object was subjected to chromatography to give 357 mg of a pale yellow solid powder, the yield rate was 41.1%.

Example 17 Preparation of Intermediate Compound 3

Weighed 600 mg of Linifanib (1.6 mmol), 324 mg of HOBT (2.4 mmol) and 460 mg of EDCl (2.4 mmol) to dissolve in 250 ml of dichloromethane, stirred the reaction for 0.5 h, controlled the reaction temperature at 20~40° C. Slowly added 3972 mg of the intermediate compound 2 (1.92 mmol) prepared in example 16, and finally DIPEA 516 mg (4.0 mmol) was added, the reaction was stirred for 12 h, and the reaction was completed by TLC (DCM/MeOH=40:1). The reaction solution was diluted with 100 ml of dichloromethane, washed twice with 250 ml of deionized water, and the organic phase was separated. The organic phase was washed with 150 ml of saturated sodium solution, separated, and dried with anhydrous sodium sulfate. The desiccant was filtered off and the filtrate was concentrated at low temperature to give a brown oily object. The oil object was subjected to silica gel column chromatography (DCM:MeOH=0:1 to 100:1) to give 1265 mg of a white solid powder; the yield rate was 32.6%.

Example 18 Preparation of Target Compound 17

1528 mg of the intermediate compound 3 (0.63 mmol) prepared in Example 17 was weighed and dissolved in 60 ml of dichloromethane, and the reaction temperature was −5 to 5° C., and 3 ml (0.04 mmol) of trifluoroacetic acid was slowly added to maintain the reaction temperature. The reaction was stirred for 20-24 h, and the reaction was completed by TLC (DCM/MeOH=40:1). The reaction solution was diluted with 40 ml of dichloromethane, washed twice with 120 ml of deionized water, twice with 60 ml of 5% sodium hydrogen carbonate solution, and twice with 120 ml of deionized water. The organic phase was separated and dried with anhydrous sodium sulfate. The desiccant was filtered off and the filtrate was concentrated at low temperature to give a red brown oily object. The oily object was subjected to chromatography to give 307 mg of a white solid powder, the yield rate was 27.6%. HPLC purity: 96.5% (214 nm), 97.7% (254 nm). MS (ESI): m/z 1765.0 [M+1]$^+$ The chemical structure is:

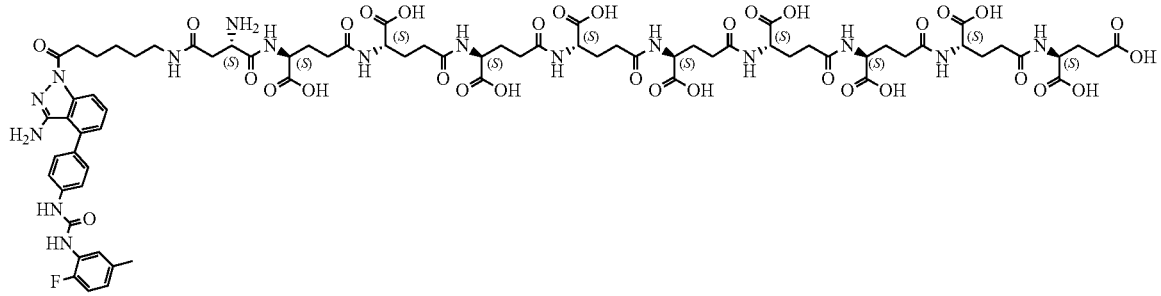

Examples 19-22: Preparation of Target Compound 7

Example 19 Preparation of Intermediate Compound 1

404 mg of Benzyl-(12-amino)dodecanoate hydrochloride (1.18 mmol), 238 mg of HOBT (1.76 mmol), and 192 mg of MCI (1.76 mmol) were weighed and dissolved in 50 ml of dichloromethane, stirred at room temperature. Controlled reaction temperature at 20~40° C. Slowly added 584 mg of Asp(Boc)-Glu(OtBu)-(OtBu) (1.23 mmol), maintained the reaction temperature, stirred the reaction for 4 h. The reaction was detected to be complete by TLC (DCM/MeOH=40:1). The reaction solution was diluted with 100 ml of dichloromethane, washed twice with 250 ml of deionized water, and the organic phase was separated. The organic phase was washed with 150 ml of saturated sodium solution, separated, and dried with anhydrous sodium sulfate. The desiccant was filtered off and the filtrate was concentrated at low temperature to give a brown oily object. This oily object was subjected to silica gel column chromatography (petroleum ether/acetone=10:1 to 2:1) to yield 278 mg of a yellow solid powder. The yield rate was 35.6%.

Example 20 Preparation of Intermediate Compound 2

2270 mg of the intermediate compound 1 (3.43 mmol) prepared in Example 19 was weighed and dissolved in 100 ml of anhydrous methanol, 10% Pd/C 50 mg was added under nitrogen atmosphere, and hydrogen was introduced and exchanged for 3 times. The reaction was controlled at 2 MPa in the atmosphere, and the reaction was carried out at 20-65° C. for 6-12 h. The reaction was completed by TLC (DCM/MeOH=40:1). The reaction solution was filtered under nitrogen atmosphere to recover palladium carbon. The filtrate was concentrated at low temperature to give a yellow brown oily object. The oily object was subjected to chromatography to give 1101 mg of a pale-yellow solid powder, and yield rate was 56.1%.

Example 21 Preparation of Intermediate Compound 3

Weighed 600 mg of Linifanib (1.6 mmol), 324 mg of HOBT (2.4 mmol), 460 mg of EDCl (2.4 mmol) in 50 ml of dichloromethane, stirred the reaction for 0.5 h, controlled the reaction temperature at 20~40° C. Slowly added 1098 mg of the intermediate compound 2 (1.92 mmol) prepared in example 4420 and finally DIPEA 516 mg (4.0 mmol) was added and the reaction was stirred for 12 h, and the reaction was completed by TLC (DCM/MeOH=40:1). The reaction solution was diluted with 100 ml of dichloromethane, washed twice with 250 ml of deionized water, and the organic phase was separated. The organic phase was washed with 150 ml of saturated sodium solution, separated, and dried with anhydrous sodium sulfate. The desiccant was filtered off and the filtrate was concentrated at low temperature to give a brown oily object. The oily object was subjected to silica gel column chromatography (DCM:MeOH=1:1 to 100:1) to give 589 mg of a white powder, and the yield rate was 39.6%.

Example 22 Preparation of Target Compound 7

Weighed 585 mg of the intermediate compound 3 (0.63 mmol) prepared in Example 21 and dissolve it in 20 ml of dichloromethane. Controlled the reaction temperature at −5~5° C. Slowly add 3 ml (0.04 mmol) of trifluoroacetic acid to maintain the reaction temperature. The reaction was stirred for 20-24 h, and the reaction was completed by TLC (DCM/MeOH=40:1). The reaction solution was diluted with 40 ml of dichloromethane, washed twice with 120 ml of deionized water, twice with 60 ml of 5% sodium hydrogen carbonate solution, and twice with 120 ml of deionized water. The organic phase was separated, and the organic phase dried with anhydrous sodium sulfate. The desiccant was filtered off and the filtrate was concentrated at low temperature to give a red brown oily object. The oily object was subjected to chromatography to give 223 mg of a white solid powder, yield rate was 43.3%. $^1$HNMR (400 MHz, DMSO-d6) δ: 9.31 (s, 1H), 8.67 (d, J=7.6 Hz, 1H) 8.59 (s, 1H), 8.31 (d, J=8.4 Hz, 1H), 8.21 (s, 1H), 8.19-7.98 (m, 4H), 7.64-7.57 (m, 3H), 7.42 (d, J=8.0 Hz, 2H), 7.19-7.09 (m, 2H), 6.83-6.82 (m, 1H), 5.18 (s, 2H), 4.29-4.13 (m, 2H), 3.12-2.96 (m, 4H), 2.73-2.68 (m, 2H), 2.67-2.63 (m, 2H), 2.28 (s, 3H), 2.12-1.67 (m, 4H), 1.37-1.23 (m, 18H). HPLC purity: 99.0% (214 nm), 99.0% (254 nm). MS (ESI): m/z 817.1 [M+1]$^+$ The chemical structure is:

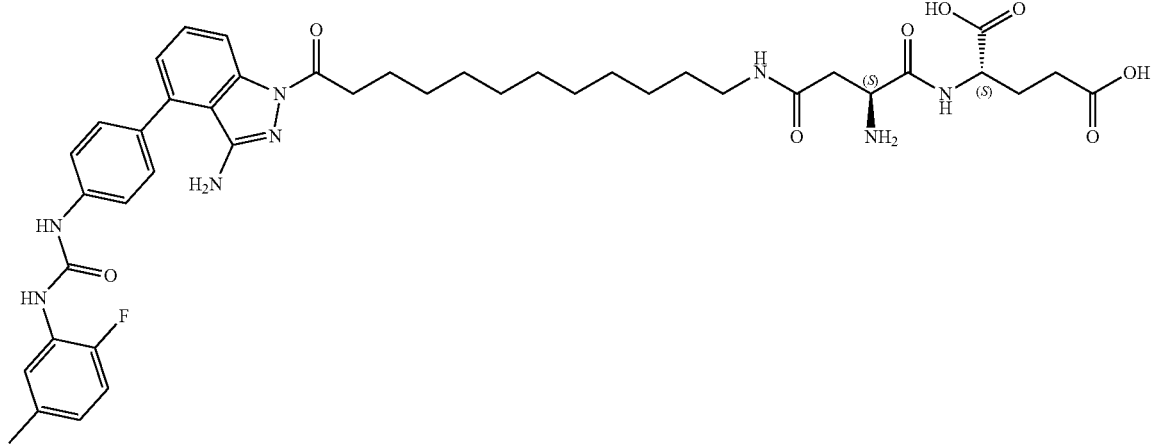

Examples 23-26: Preparation of Target Compound 8 (Linifanib-C$_{12}$-AA$_5$)

Example 23 Preparation of Intermediate Compound 1

404 mg of Benzyl-(12-amino)dodecanoate hydrochloride (1.18 mmol), 238 mg of HOBT (1.76 mmol), and 192 mg of EDCl (1.76 mmol) were weighed and dissolved in 250 ml of dichloromethane, stirred at room temperature. Controlled reaction temperature at 20~40° C. Slowly added 1267 mg of Asp(Boc)-Glu(OtBu)-Glu(OtBu)-Glu(OtBu)-Glu(OtBu)-(OtBu) (1.23 mmol), and maintained the reaction temperature. Stir-reacted for 4 h, and the reaction was completed by TLC (DCM/MeOH=40:1). The reaction solution was diluted with 100 ml of dichloromethane, washed twice with 250 ml of deionized water, and the organic phase was separated. The organic phase was washed with 150 ml saturated sodium solution, separated, and dried with anhydrous sodium sulfate. The desiccant was filtered off and the filtrate was concentrated at low temperature to give a brown oily object. The oily object was subjected to silica gel column chromatography (petroleum ether/acetone=10:1 to 2:1) to give 553 mg of a yellow solid powder, the yield rate was 35.6%.

Example 24 Preparation of Intermediate Compound 2

Weighed 4000 mg (3.0 mmol) of the intermediate compound 1 prepared in Example 23, dissolved in 100 ml of anhydrous methanol, 10% Pd/C 50 mg under nitrogen atmosphere, and replaced with hydrogen for 3 times. The reaction was controlled at 2 MPa in the atmosphere, and the reaction was carried out at 20-65° C. for 6-12 h. The reaction was completed by TLC (DCM/MeOH=40:1). The reaction solution was filtered under nitrogen atmosphere to recover palladium carbon. The filtrate was concentrated at low temperature to give a yellow brown oily object. The oily object was subjected to chromatography to give 1595 mg of a pale-yellow solid powder, the yield rate was 42.8%.
$^1$HNMR (CDCl$_3$) δ1.27 (brs, 14H), 1.46~1.47 (m, 54H), 1.65~1.85 (m, 8H), 2.34~2.35 (brs, 16H), 3.06~3.36 (brs, 2H), 4.46-4.52 (m, 5H), 6.31 (brs, 1H, —NH—C=O), 6.68 (brs, 1H, —NH—C=O), 6.91 (brs, 2H, —NH—C=O), 7.19 (brs, 1H, —NH—C=O), 7.54 (brs, 1H, —NH—C=O). $^{13}$CNMR (CDCl$_3$) δ 192.97, 190.34, 173.02, 172.22, 172.00, 171.81, 171.22, 171.08, 170.76, 82.42, 82.27, 82.08, 82.02, 80.64, 80.53, 52.35, 51.83, 51.44, 39.84, 33.79, 32.52, 32.15, 31.61, 31.11, 29.26, 29.11, 28.97, 28.92, 28.86, 28.78, 28.71, 28.48, 28.33, 28.10, 28.01, 27.98, 27.76, 27.65, 26.68, 24.61, 12.10.

The chemical structure is:

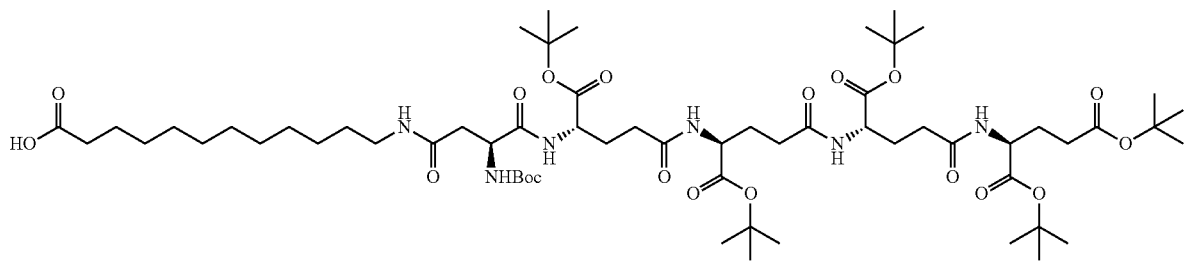 [SMILES: CC(C)(C)OC(=O)CC[C@H](NC(=O)CC[C@H](NC(=O)CC[C@H](NC(=O)CC[C@H](NC(=O)[C@H](CC(=O)NCCCCCCCCCCCC(=O)O)NC(=O)OC(C)(C)C)C(=O)OC(C)(C)C)C(=O)OC(C)(C)C)C(=O)OC(C)(C)C)C(=O)OC(C)(C)C]

Example 25 Preparation of Intermediate Compound 3

Weighed 600 mg of Linifanib (1.6 mmol), 324 mg of HOBT (2.4 mmol), and 460 mg of EDCl (2.4 mmol) to dissolve in 250 ml of dichloromethane, stirred the reaction for 0.5 h, controlled the reaction temperature at 20~40° C. Slowly added 2340 mg (1.9 mmol) of the intermediate compound 2 prepared in example 24 and finally DIPEA 516 mg (4.0 mmol) was added, the reaction was stirred for 12 h, and the reaction was completed by TLC (DCM/MeOH=40:1). The reaction solution was diluted with 100 ml of dichloromethane, washed twice with 250 ml of deionized water, and the organic phase was separated. The organic phase was washed with 150 ml of saturated sodium solution, separated, and dried with anhydrous sodium sulfate. The desiccant was filtered off and the filtrate was concentrated at low temperature to give a brown oily object. The oily object was subjected to silica gel column chromatography (DCM:MeOH=0:1 to 100:1) to give 1132 mg of a white solid powder; the yield rate was 44.7%.

Example 26 Preparation of Target Compound 8 (Linifanib-$C_{12}$-$AA_5$)

Weighed 1000 mg (0.63 mmol) of the intermediate compound 3 prepared in Example 25 and dissolved it in 60 ml of dichloromethane, and slowly added 3 ml (0.04 mmol) of trifluoroacetic acid at a reaction temperature of −5 to 5° C. to maintain the reaction temperature. The reaction was stirred for 20-24 h, and the reaction was completed by TLC (DCM/MeOH=40:1). The reaction solution was diluted with 40 ml of dichloromethane, washed twice with 120 ml of deionized water, twice with 60 ml of 5% sodium hydrogen carbonate solution, and twice with 120 ml of deionized water. The organic phase was separated, and the organic phase dried with anhydrous sodium sulfate. The desiccant was filtered off and the filtrate was concentrated at low temperature to give a red brown oily object. The oily object was subjected to chromatography to give 293 mg of a white solid powder, yield rate was 38.6%. $^1$HNMR (400 MHz, DMSO-d6) δ: 9.51 (s, 1H), 8.97 (s, 1H), 8.56 (s, 1H), 8.32 (d, J=8.4 Hz, 1H), 8.18 (s, 1H), 8.02-7.96 (m, 4H), 7.66-7.57 (m, 3H), 7.42 (d, J=8.8 Hz, 2H), 7.19-7.08 (m, 2H), 6.82-6.81 (m, 1H), 5.18 (s, 2H), 4.16-3.98 (m, 6H), 3.07-2.96 (m, 4H), 2.67-2.63 (m, 2H), 2.28 (s, 3H), 2.24-2.14 (m, 8H), 2.03-1.87 (m, 5H), 1.77-1.67 (m, 4H), 1.37-1.23 (m, 18H). HPLC purity: 99.3% (214 nm), 99.1% (254 nm). MS (HI): m/z 1204.5 $[M+1]^+$ The chemical structure is:

Examples 27-30: Preparation of Target Compound 9

Example 27 Preparation of Intermediate Compound 1

404 mg (1.18 mmol) of Benzyl-(12-amino)dodecanoate hydrochloride, 238 mg (1.76 mmol) of HOBT, and 192 mg (1.76 mmol) of MCI were weight and dissolved in 250 ml of dichloromethane, stirred at room temperature. Controlled reaction temperature at 20~40° C. Slowly added 2406 mg (1.23 mmol) of Asp(Boc)-Glu(OtBu)-Glu(OtBu)-Glu(OtBu)-Glu(OtBu)-Glu(OtBu)-Glu(OtBu)-Glu(OtBu)-Glu(OtBu)-Glu(OtBu)-(OtBu), maintained the reaction temperature and stir-reacted for 4 h, and the reaction was completed by TLC (DCM/MeOH=40:1). The reaction solution was diluted with 100 ml of dichloromethane, washed twice with 250 ml of deionized water, and the organic phase was separated. The organic phase was washed with 150 ml saturated sodium solution, separated, and dried with anhydrous sodium sulfate. The desiccant was filtered off and the filtrate was concentrated at low temperature to give a brown oily object. This oily object was subjected to silica gel column chromatography (petroleum ether/acetone=10:1 to 2:1) to yield 627 mg of a yellow solid powder, yield rate was 23.7%.

Example 28 Preparation of Intermediate Compound 2

6732 mg (3.0 mmol) of the intermediate compound 1 prepared in Example 27 was weighed and dissolved in 200 ml of anhydrous methanol, 10% Pd/C 50 mg was added under nitrogen atmosphere, and hydrogen was introduced and exchanged for 3 times. The reaction was controlled at 2 MPa in the atmosphere, and the reaction was carried out at 20-65° C. for 6-12 h. The reaction was completed by TLC (DCM/MeOH=40:1). The reaction solution was filtered under nitrogen atmosphere to recover palladium carbon. The filtrate was concentrated at low temperature to give a yellow brown oily object. The oily object was subjected to chromatography to give 2480 mg of a pale-yellow solid powder, yield rate was 38.4%.

Example 29 Preparation of Intermediate Compound 3

Weighed 600 mg (1.6 mmol) of Linifanib, 324 mg (2.4 mmol) of HOBT and 460 mg (2.4 mmol) of EDCl, and dissolved in 250 ml of dichloromethane, stirred the reaction

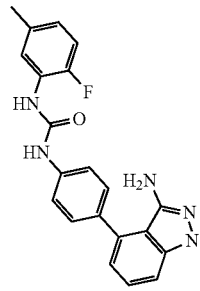
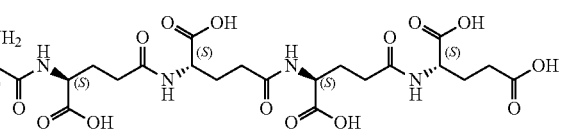

Linifanib-$C_{12}$-$AA_5$ for 0.5 h, controlled the reaction temperature at 20~40° C. Slowly added 4134 mg (1.92 mmol) of intermediate compound 2 prepared in example 28 and finally DIPEA 516 mg (4.0 mmol) was added, the reaction was stirred for 12 h, and the reaction was completed by TLC (DCM/MeOH=40:1). The reaction solution was diluted with 100 ml of dichloromethane, washed twice with 250 ml of deionized water, and the organic phase was separated. The organic phase was washed with 150 ml of saturated sodium solution, separated, and dried with anhydrous sodium sulfate. The desiccant was filtered off and the filtrate was concentrated at low temperature to give a brown oily object. The oily object was subjected to silica gel column chromatography (DCM:MeOH=1:1 to 100:1) to give 1152 mg of a white solid powder, and the yield rate was 28.7%.

Example 30 Preparation of Target Compound 9

Weighed 1581 mg (0.63 mmol) of the intermediate compound 3 prepared in Example 29, dissolved in 60 ml of dichloromethane, and slowly added 3 ml (0.04 mmol) of trifluoroacetic acid at a reaction temperature of −5 to 5° C. to maintain the reaction temperature. The reaction was stirred for 20-24 h, and the reaction was completed by TLC (DCM/MeOH=40:1). The reaction solution was diluted with 40 ml of dichloromethane, washed twice with 120 ml of deionized water, twice with 60 ml of 5% sodium hydrogen carbonate solution, and twice with 120 ml of deionized water. The organic phase was separated, and the organic phase dried with anhydrous sodium sulfate. The desiccant was filtered off and the filtrate was concentrated at low temperature to give a red brown oily object. The oily object was subjected to chromatography to give 274 mg of a white solid powder, yield rate was 23.5%. HPLC purity: 93.2% (214 nm), 94.5% (254 nm). MS (ESI): m/z 1849.7 [M+1]$^+$ Chemical structure is:

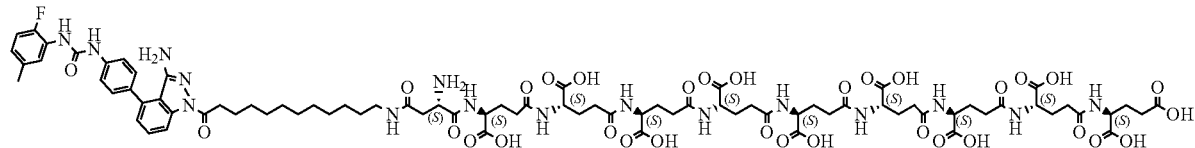

Experiments 31-33: Preparation of Target Compound 10

Example 31 Preparation of Metabolite Intermediate Compound Mc

Weighed 137 mg (0.42 mmol) of Boc-L-aspartic acid 1-benzyl ester, 77.8 mg (0.58 mmol) of HOBT, and 110 mg (0.58 mmol) of EDCl and dissolved in 10 ml of dichloromethane, stirred the reaction for 0.5 h, controlled a reaction temperature of 20 to 40° C. 143 mg (0.38 mmol) of Linifanib was slowly added and finally DIPEA 124 mg (0.96 mmol) was added. After the addition, the reaction temperature was maintained for 4 h, and the reaction was completed by TLC (DCM/MeOH=40:1). The reaction mixture was diluted with 50 ml of methylene chloride and washed twice with 100 ml of deionized water. The desiccant was filtered off and the filtrate was concentrated at low temperature to give a brown oily object. The oily object was subjected to silica gel column chromatography (DCM:MeOH=1:1 to 30:1) to give 221 mg of a yellow oily object, the yield rate was 77.3%.

Example 32 Preparation of Metabolite Intermediate Compound Md 198 mg (0.29 mmol) of the intermediate compound Mc prepared in Example 31 was weighed and dissolved in 20 ml of dichloromethane, and the reaction temperature was −5 to 5° C., and 3 ml (0.04 mmol) of trifluoroacetic acid was slowly added to maintain the reaction temperature. The reaction was stirred for 1.5 to 2 h, and the reaction was completed by TLC (DCM/MeOH=40:1). The reaction solution was diluted with 50 ml of dichloromethane, washed twice with 120 ml of deionized water, twice with 60 ml of 5% sodium hydrogen carbonate solution, and twice with 120 ml of deionized water. The organic phase was separated and dried with anhydrous sodium sulfate. The desiccant was filtered off and the filtrate was concentrated to a yellow oily object. The oily object was chromatographed to give 131 mg of a yellow oily object, the yield rate was 77.8%.

Example 33 Preparation of Target Compound 10

336 mg (0.58 mmol) of the intermediate Md prepared in Example 32 was weighed and dissolved in 30 ml of anhydrous methanol, and 10% Pd/C 25 mg was added under nitrogen atmosphere, and hydrogen was introduced and exchanged for 3 times. The reaction was controlled at 2 MPa in the atmosphere, the reaction was carried out at 20~65° C. for 6~12 h, and the reaction was completed by TLC (DCM/MeOH=40:1). The reaction solution was filtered under nitrogen atmosphere to recover palladium carbon. The filtrate was concentrated at low temperature to give a pale-yellow oily object. The oily object was subjected to chromatography to give 178 mg of a white solid powder, yield rate was 62.6%. HPLC purity: 97.2% (214 nm), 98.6% (254 nm). MS (ESI): m/z 491.0[M+1]$^+$ The chemical structure is:

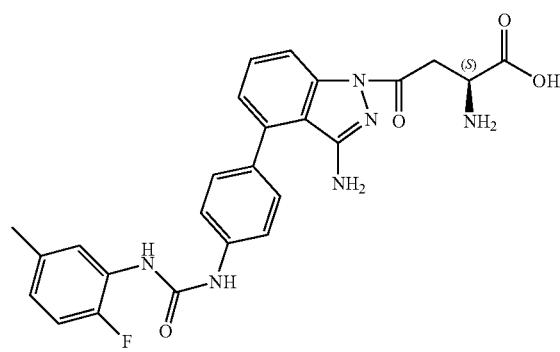

Examples 34-38: Preparation of Target Compound 11

Example 34 Preparation of Metabolite Intermediate Compound Ma 136 mg (0.59 mmol) of 6-(BOC-amino)hexane acid, 107 mg (0.8 mmol) of HOBT, and 152 mg (0.8 mmol) of EDCl were weighed and dissolved in 10 ml of dichloromethane, stirred the reaction for 0.5 h, controlled the reaction temperature at 20~40° C. 200 mg (0.53 mmol) of Linifanib was slowly added and finally DIPEA 171 mg (1.3 mmol) was added. After the addition, the reaction temperature was maintained and stir-reacted for 4 h, and the reaction was completed by TLC (DCM/MeOH=40:1). The reaction mixture was diluted with 50 ml of methylene chloride and washed twice with 100 ml of deionized water, and the organic phase was separated and dried with anhydrous sodium sulfate. The desiccant was filtered off and the filtrate was concentrated at low temperature to give a brown oily object. The oily object was subjected to silica gel column chromatography (DCM:MeOH=1:1 to 30:1) to give 207 mg of a yellow oily object, and the yield rate was 59.8%.

Example 35 Preparation of Metabolite Intermediate Compound Mb 194 mg (0.33 mmol) of the intermediate Ma prepared in Example 34 was weighed and dissolved in 20 ml of dichloromethane, and the reaction temperature was a −5 to 5° C., and 3 ml (0.04 mmol) of trifluoroacetic acid was slowly added; the reaction temperature was maintained and stir-reacted for 1.5~2 h, and the reaction was completed by TLC (DCM/MeOH=40:1). The reaction solution was diluted with 50 ml of dichloromethane, washed twice with 120 ml of deionized water, twice with 60 ml of 5% sodium hydrogen carbonate solution, and twice with 120 ml of deionized water. The organic phase was separated and dried with anhydrous sodium sulfate. The desiccant was filtered off and the filtrate was concentrated at low temperature to give a red brown oily object. The oily object was subjected to chromatography to give 147 mg of a yellow oily object, the yield rate was 91.1%.

Example 36 Preparation of Metabolite Intermediate Compound Mc 137 mg (0.42 mmol) of Boc-L-aspartic acid 1-benzyl ester, 77.8 mg (0.58 mmol) of HOBT and 110 mg (0.58 mmol) EDCl were weighed and dissolved in 10 ml of dichloromethane, stirred the reaction for 0.5 h, controlled the reaction temperature at 20 to 40° C. 185 mg (0.38 mmol) of the intermediate Mb prepared in Example 35 was slowly added, and finally DIPEA 124 mg (0.96 mmol) was added. After the addition, the reaction temperature was maintained and stir-reacted for 4 h, the reaction was completed by TLC (DCM/MeOH=40:1). The reaction mixture was diluted with 50 ml of methylene chloride and washed twice with 100 ml of deionized water. The desiccant was filtered off and the filtrate was concentrated at low temperature to give a brown oily object. The oily object was subjected to silica gel column chromatography (DCM:MeOH=1:1 to 30:1) to give 200 mg of a yellow oily object, the yield rate was 66.3%.

Example 37 Preparation of Metabolite Intermediate Compound Md 230 mg (0.29 mmol) of the intermediate compound Mc prepared in Example 36 was weighed and dissolved in 20 ml of dichloromethane, and the reaction temperature was controlled at −5 to 5° C. Slowly add 3 ml (0.04 mmol) of trifluoroacetic acid to maintain the reaction temperature. The reaction was stirred for 1.5 to 2 h, and the reaction was completed by TLC (DCM/MeOH=40:1). The reaction solution was diluted with 50 ml of dichloromethane, washed twice with 120 ml of deionized water, twice with 60 ml of 5% sodium hydrogen carbonate solution, and twice with 120 ml of deionized water. The organic phase was separated and dried with anhydrous sodium sulfate. The desiccant was filtered off and the filtrate was concentrated to a yellow oily object. The oily object was subjected to chromatography to give 158 mg of a yellow oily object, the yield rate was 78.4%.

Example 38 Preparation of Target Compound 11

425 mg (0.61 mmol) of the intermediate Md prepared in Example 37 was weighed and dissolved in 30 ml of anhydrous methanol, and 10% Pd/C 25 mg was added under nitrogen atmosphere, and hydrogen was introduced and exchanged for 3 times. The reaction was controlled at 2 MPa in the atmosphere, the reaction was carried out at 20~65° C. for 6~12 h, and the reaction was completed by TLC (DCM/MeOH=40:1). The reaction solution was filtered under nitrogen atmosphere to recover palladium carbon. The filtrate was concentrated at low temperature to give a pale-yellow oily object. The oily object was subjected to p chromatography to give 234 mg of a white solid powder, and the yield rate was 63.4%. HPLC purity: 96.2% (214 nm), 98.1% (254 nm). MS (ESI): m/z 604.3[M+1]$^+$ The chemical structure is:

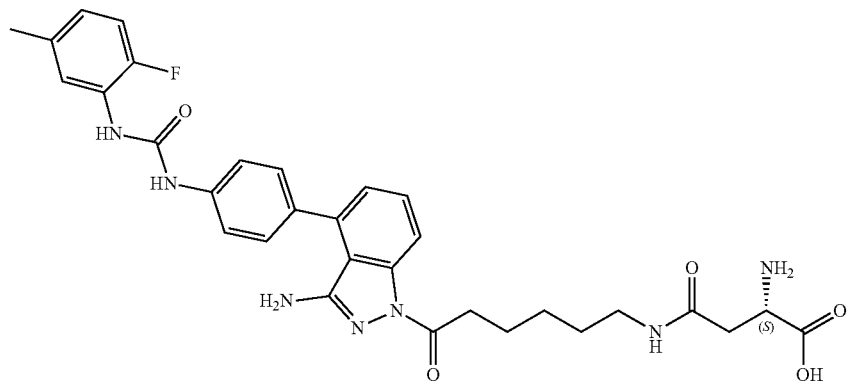

Examples 39-43: Preparation of Target Compound 12 (Linifanib-C12-Asp)

Example 39 Preparation of Metabolite Intermediate Compound Ma 186 mg (0.59 mmol) of 12-(BOC-amino)dodecanoic acid, 107 mg (0.8 mmol) of HOBT and 152 mg (0.8 mmol) of EDCl were weighed and dissolved in 10 ml of dichloromethane, stirred the reaction for 0.5 h, controlled the reaction temperature at 20~40° C. Slowly added 200 mg (0.53 mmol) of Linifanib and finally added DIPEA 171 mg (1.3 mmol). The reaction temperature was maintained and stir-reacted for 4 hr. The reaction was completed by TLC (DCM/MeOH=40:1). The reaction mixture was diluted with 50 ml of methylene chloride and washed twice with 100 ml of deionized water. The desiccant was filtered off and the filtrate was concentrated at low temperature to give a brown oily object. The oily object was subjected to silica gel column chromatography (DCM:MeOH=1:1 to 30:1) to give 225 mg of a yellow oily object, and the yield rate was 63.2%.

Example 40 Preparation of Metabolite Intermediate Compound Mb 225 mg (0.33 mmol) of the intermediate Ma prepared in Example 39 was weighed and dissolved in 20 ml of dichloromethane, and the reaction temperature was −5 to 5° C. 3 ml (0.04 mmol) of trifluoroacetic acid was slowly added to maintain the reaction temperature. Stir-reacted for 1.5~2 h, and the reaction was completed by TLC (DCM/MeOH=40:1). The reaction solution was diluted with 50 ml of dichloromethane, washed twice with 120 ml of deionized water, twice with 60 ml of 5% sodium hydrogen carbonate solution, and twice with 120 ml of deionized water. The organic phase was separated and dried with anhydrous sodium sulfate. The desiccant was filtered off and the filtrate was concentrated at low temperature to give a red brown oily object. The oily object was chromatographed to give 220 mg of a yellow oily object, the yield rate was 95%.

Example 41 Preparation of Metabolite Intermediate Compound Mc 137 mg (0.42 mmol) of Boc-L-aspartic acid 1-benzyl ester, 77.8 mg (0.58 mmol) of HOBT, and 110 mg (0.58 mmol) of EDCl were weighed and dissolved in 10 ml of dichloromethane, stirred the reaction for 0.5 h, controlled the reaction temperature of 20 to 40° C. 220 mg (0.38 mmol) of the intermediate Mb prepared in Example 40 was slowly added at finally DIPEA 124 mg (0.96 mmol) was added. The reaction was stirred for 4 h and completed by TLC (DCM/MeOH=40:1). The reaction mixture was diluted with 50 ml of methylene chloride and washed twice with 100 ml of deionized water. The desiccant was filtered off and the filtrate was concentrated at low temperature to give a brown oily object. The oily object was subjected to silica gel column chromatography (DCM:MeOH=1:0-30:1) to give 250 mg of a yellow oily object, the yield rate was 74.2%.

Example 42 Preparation of Metabolite Intermediate Compound Md 250 mg (0.29 mmol) of the intermediate compound Mc prepared in Example 41 was weighed and dissolved in 20 ml of dichloromethane, and slowly added 3 ml (0.04 mmol) of trifluoroacetic acid at a reaction temperature of −5 to 5° C. to maintain the reaction temperature. The reaction was stirred for 1.5 to 2 h, and the reaction was completed by TLC (DCM/MeOH=40:1). The reaction solution was diluted with 50 ml of dichloromethane, washed twice with 120 ml of deionized water, twice with 60 ml of 5% sodium hydrogen carbonate solution, and twice with 120 ml of deionized water. The organic phase was separated and dried with anhydrous sodium sulfate. The desiccant was filtered off and the filtrate was concentrated to a yellow oily object. The oily object was subjected to chromatography to give 158 mg of a yellow oily object, the yield rate was 71%.

Example 43 Preparation of Target Compound 12 (Linifanib-$C_{12}$-Asp)

210 mg of the intermediate Md prepared in Example 42 was weighed and dissolved in 30 ml of anhydrous methanol, added 10% Pd/C 25 mg under nitrogen protection, hydrogen was introduced and exchanged for three times, and the reaction was controlled at 2 MPa in the atmosphere. The reaction was carried out at 20~65° C. for 6~12 h, and the reaction was completed by TLC (DCM/MeOH=40:1). The reaction solution was filtered under nitrogen atmosphere to recover palladium carbon. The filtrate was concentrated at low temperature to give a pale-yellow oily object. The oily object was subjected to chromatography to give 102 mg of a white solid powder, and the yield rate was 54.8%. $^1$HNMR (DMSO) δ: 1.22 (m, 12H), 1.35 (m, 4H), 1.71 (s, 2H), 2.41 (s, 3H, —CH3), 2.64 (m, 1H), 2.72 (m, 1H), 3.34 (m, 6H), 3.50 (m, 2H), 5.20 (s, 2H), 6.83 (brs, 1H), 7.10 (m, 1H), 7.18 (m, 1H), 7.40 (d, J=7.5 Hz, 2H), 7.58 (m, 1H), 7.67 (d, J=7.5 Hz, 2H), 7.91 (m, 1H), 8.23 (m, 1H), 8.32 (m, 1H), 9.01 (m, 1H), 9.83 (m, 1H). HPLC purity: 98.5% (214 nm), 99.3% (254 nm). MS (ESI): m/z 688.4[M+1]$^+$ The chemical structure is:

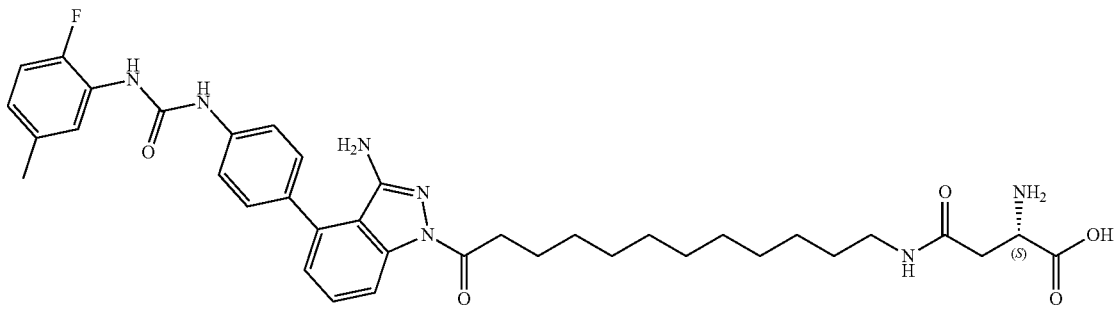

Linifanib-$C_{12}$-Asp

Example 44 Effect of Linifanib Related Compounds on the Proliferation of Tumor Cell Lines This application measured the half-inhibitory concentration (IC50 value) of 13 compounds (Compound 1-12 and Linifanib on 54 commercial tumor cell lines (including 26 liver cancer cell lines) by cell proliferation assay (Alamar Blue assay platform). The difference between the 12 compounds and the active drug Linifanib activity was compared.

1. Instruments and Materials

Thermo 311 $CO_2$ incubator; Haier biosafety cabinet; Molecular Devices microplate reader; Xiangyi brand L530 desktop low speed centrifuge; Olympus IX51 inverted fluorescence microscope, DMEM, RPMI 1640, MEM, DMEM/F12 1:1 medium, Fetal bovine serum, 0.25% trypsin solution, phosphate buffer (Thermo Fisher Shanghai Co., Ltd.); sigma dimethyl sulfoxide (DMSO), resazurin; 54 commercial tumor cell lines (including 26 liver cancer cell lines). Experimental drugs: compounds 1-12 and active drug Linifanib; chemotherapeutic drug Doxorubicin (HY-15142; Shanghai Qianyuan Biomedical Technology Co., Ltd.).

2. Experimental Methods 2.1 Cultivation of different cell lines 54 cell lines were cultured in a culture medium containing fetal bovine serum and placed in a 5% CO 2 incubator at 37° C. for incubation. The cells were all grown in an adherent state, and the growth was observed under an inverted microscope, and subculture was performed when the cell confluence rate reached 80%-90%. The proportion and quantity of passage were determined by experimental needs. The ratio of subculture of this cell line was generally 1:2~1:3.

2.2 inhibition effect on the proliferation of different tumor cell lines

Cell test: 54 cell lines in logarithmic growth phase were inoculated in 96-well culture plates at 500~1×104/well (the optimal seeding density of each cell line was determined in pre-experiment), After incubating at 37° C. for 4 h in a 5% $CO_2$ humidification incubator, added 10 μL of compounds 1-12 or Linifanib to each well, and tested 9 drug concentration gradients for each compound (diluted from the highest concentration of the test by 3.16 times). The solubility of each compound was different at a starting concentration of 30 or 100 μM, respectively. The QC reference compound Doxorubicin was added simultaneously to each cell line test, and the final drug concentrations were 10, 3.16, 1, 0.31, 0.1, 0.03, 0.01, 0.003, and 0.001 μM, respectively. In addition, a positive control group (100% inhibition) and a negative control group (0% inhibition) were set at the same time. The drug group was repeated for 2 wells per concentration, and the positive control group and the negative control group were repeated for 6 wells. After the culture was continued for 6 days in the incubator, AlamarBlue test operation was followed;

AlamarBlue test procedure: Incubated with 10 μL of AlamarBlue reagent per well for 1-4 h, shook for 1-2 min, MD microplate reader EX: 560 nm, EM: 590 nm wavelength to measure fluorescence, recorded the results, calculated the cell inhibition rate of the compound of the invention. Cell inhibition rate (%)= (A0% inhibition−A administration)/(A0% inhibition−A100% inhibition)×100%, and then using the method of nonlinear regression using Graph Pad Prism 5.0 or MATILAB software (usually using four parameters) to graph and obtain a drug dose response curve to obtain an IC50 value of the compound of the present invention acting on a cancer cell line.

3. Results and Analysis 3.1 The IC50 summary results of 13 test samples (compounds 1-12 and Linifanib) on 54 commercial tumor cell lines are shown in Table 1.

TABLE 1

Summary of IC50 (μM) values of six compounds against 54 commercial tumor cell lines

| Tumor cell line number | Tumor cell line name | Compound 8 (Linifanib-$C_{12}$-AA$_5$) | Compound 12 (Linifanib-$C_{12}$-Asp) | Compound 1 | Compound 4 | Compound 7 | Linifanib |
|---|---|---|---|---|---|---|---|
| 1 | 22RV1 | >100 | >30 | 6.69 | >100 | >100 | 7.50 |
| 2 | AN3CA | 3.14 | 2.08 | 0.31 | 28.65 | 2.94 | 0.19 |
| 3 | CCRF-CEM | >100 | >30 | 2.50 | 51.66 | 14.96 | 5.03 |
| 4 | DLD1 | 51.06 | >30 | 9.86 | >100 | 96.96 | 11.59 |
| 5 | DU145 | 20.69 | >30 | 2.76 | 37.98 | 17.19 | 5.01 |
| 6 | HCCLM3 | >100 | >30 | 11.43 | 82.04 | >100 | 6.67 |
| 7 | HT1080 | 45.26 | >30 | 13.19 | >100 | >100 | 6.40 |
| 8 | HT55 | >100 | >30 | 16.75 | >100 | >100 | 22.29 |
| 9 | HuTu80 | 43.78 | >30 | 3.17 | 38.25 | 21.05 | 1.85 |
| 10 | K562 | >100 | >30 | 3.99 | 44.16 | 23.95 | 10.85 |
| 11 | KASUMI-1 | 0.10 | 0.05 | 0.051 | 1.713 | 0.096 | 0.01 |
| 12 | KM12 | 12.38 | >30 | 1.89 | 33.88 | 7.72 | 1.39 |
| 13 | LC-2-ad | 50.25 | >30 | 8.89 | 36.85 | 54.26 | 4.78 |
| 14 | LNCAP-clone-FGC | >100 | >30 | 5.47 | 75.34 | 26.66 | 11.30 |
| 15 | MDA-MB-231 | 53.51 | >30 | 3.95 | 96.51 | 32.07 | 4.03 |
| 16 | MDA-MB-435S | 38.49 | >30 | 18.87 | 98.81 | >100 | 10.71 |
| 17 | MFM-223 | 23.97 | >30 | 8.89 | 37.95 | 24.10 | 1.72 |

TABLE 1-continued

Summary of IC50 (μM) values of six compounds against 54 commercial tumor cell lines

| Tumor cell line number | Tumor cell line name | Compound 8 (Linifanib-$C_{12}$-$AA_5$) | Compound 12 (Linifanib-$C_{12}$-Asp) | Compound 1 | Compound 4 | Compound 7 | Linifanib |
|---|---|---|---|---|---|---|---|
| 18 | MG63 | 37.23 | >30 | 7.69 | 94.52 | 72.96 | 1.78 |
| 19 | NCI-H1648 | >100 | >30 | 6.89 | >100 | >100 | 7.17 |
| 20 | NCI-H1703 | 0.08 | 0.05 | 0.04 | 1.59 | 0.18 | 0.02 |
| 21 | NCI-H2170 | 51.93 | >30 | 0.97 | 83.99 | 22.54 | 4.00 |
| 22 | NCI-H526 | 100.00 | >30 | 6.60 | >100 | >100 | 7.80 |
| 23 | NCI-H661 | >100 | >30 | 7.09 | 99.50 | 86.73 | 13.34 |
| 24 | NCI-H716 | 26.88 | >30 | 1.82 | 43.75 | 8.45 | 4.10 |
| 25 | SW620 | 44.47 | >30 | 2.79 | 71.44 | 21.92 | 2.78 |
| 26 | T.T | >100 | >30 | 5.22 | >100 | >100 | 4.86 |
| 27 | TE-15 | 42.74 | >30 | 7.59 | >100 | 63.57 | 3.60 |
| 28 | TE-6 | >100 | >30 | 4.29 | >100 | 74.34 | 4.09 |
| 29 | Li-7 | 39.55 | >30 | 5.35 | 47.24 | 34.46 | 5.43 |
| 30 | JHH1 | 35.42 | >30 | 8.15 | >100 | >100 | 12.16 |
| 31 | JHH2 | >100 | >30 | 28.93 | >100 | >100 | 29.54 |
| 32 | JHH4 | 95.87 | >30 | 2.62 | 42.53 | 39.44 | 10.61 |
| 33 | JHH5 | 48.64 | >30 | 15.21 | >100 | >100 | 10.04 |
| 34 | JHH6 | 41.72 | >30 | 3.00 | 67.74 | 23.58 | 4.11 |
| 35 | JHH7 | 20.65 | >30 | 1.81 | 45.90 | 9.98 | 1.83 |
| 36 | HUH1 | 31.86 | >30 | 4.42 | 66.83 | 21.21 | 3.25 |
| 37 | HUH6 | 28.23 | 10.57 | 0.13 | 53.79 | >100 | >30 |
| 38 | HUH7 | 23.60 | >30 | 3.22 | 60.04 | 22.05 | 1.67 |
| 39 | Hep3B2.1-7 | 36.22 | >30 | 1.59 | 69.84 | 13.00 | 1.96 |
| 40 | HEPG2 | 21.44 | >30 | 0.45 | 19.00 | 5.83 | 0.83 |
| 41 | HLE | 36.84 | >30 | 1.98 | 47.52 | 36.30 | 3.93 |
| 42 | HLF | 44.55 | >30 | 3.98 | 52.55 | 24.41 | 3.65 |
| 43 | Alexander cells | >100 | >30 | 5.50 | 97.15 | 98.04 | 4.09 |
| 44 | SK-HEP-1 | >100 | >30 | 4.59 | 63.99 | 29.18 | 7.11 |
| 45 | SNU182 | >100 | 19.50 | 19.88 | >100 | >100 | 15.16 |
| 46 | SNU354 | 40.58 | >30 | 3.91 | 78.78 | 30.18 | 4.58 |
| 47 | SNU387 | 90.22 | 30.32 | 12.79 | >100 | >100 | 12.32 |
| 48 | SNU398 | 50.06 | >30 | 2.61 | 96.51 | 18.13 | 1.91 |
| 49 | SNU423 | 36.88 | 10.89 | 9.03 | >100 | >100 | 9.24 |
| 50 | SNU449 | 60.29 | >30 | 5.21 | >100 | 31.63 | 10.19 |
| 51 | SNU475 | 57.46 | >30 | 4.85 | 81.33 | 40.68 | 5.37 |
| 52 | SNU739 | 64.93 | >30 | 4.56 | 73.81 | 37.40 | 5.45 |
| 53 | SNU761 | 80.13 | >30 | 9.53 | 85.01 | >100 | 8.98 |
| 54 | SNU886 | 60.95 | >30 | 1.47 | 96.17 | 22.02 | 4.48 |

Note:
cell lines 29-54 in Table 1 show the responses of liver cancer cell lines to each compound.

TABLE 2

Summary of IC50 (μM) values of seven compounds against 54 commercial tumor cell lines

| Tumor cell line number | Tumor cell line name | Compound 2 | Compound 3 | Compound 5 | Compound 6 | Compound 9 | Compound 10 | Compound 11 |
|---|---|---|---|---|---|---|---|---|
| 1 | 22RV1 | 7.81 | 10.32 | >100 | >100 | >100 | 6.21 | 90.12 |
| 2 | AN3CA | 0.45 | 0.64 | 45.63 | 55.37 | 8.42 | 0.24 | 20.15 |
| 3 | CCRF-CEM | 6.33 | 10.25 | 70.32 | 90.47 | 30.19 | 1.74 | 40.74 |
| 4 | DLD1 | 13.97 | 20.33 | >100 | >100 | >100 | 7.53 | 88.39 |
| 5 | DU145 | 4.89 | 7.38 | 55.37 | 63.26 | 34.51 | 1.34 | 26.38 |
| 6 | HCCLM3 | 15.75 | 25.67 | >100 | >100 | >100 | 8.97 | 74.26 |
| 7 | HT1080 | 19.29 | 25.79 | >100 | >100 | >100 | 8.82 | 94.37 |
| 8 | HT55 | 20.45 | 31.31 | >100 | >100 | >100 | 14.87 | >100 |
| 9 | HuTu80 | 5.62 | 7.33 | 48.44 | 61.04 | 73.46 | 2.63 | 23.09 |
| 10 | K562 | 7.13 | 16.94 | 56.05 | 74.33 | >100 | 3.04 | 33.35 |
| 11 | KASUMI-1 | 0.12 | 0.19 | 3.21 | 4.94 | 0.23 | 0.042 | 1.21 |
| 12 | KM12 | 2.94 | 4.63 | 45.69 | 70.02 | 21.79 | 1.47 | 28.54 |
| 13 | LC-2-ad | 13.46 | 22.37 | 51.28 | 67.81 | 70.52 | 6.38 | 27.49 |
| 14 | LNCAP-clone-FGC | 6.34 | 15.38 | >100 | >100 | >100 | 5.13 | 70.91 |
| 15 | MDA-MB-231 | 5.02 | 8.51 | >100 | >100 | 81.09 | 3.17 | 80.36 |
| 16 | MDA-MB-435S | 30.01 | 46.36 | >100 | >100 | >100 | 13.34 | 87.63 |

TABLE 2-continued

Summary of IC50 (μM) values of seven compounds against 54 commercial tumor cell lines

| Tumor cell line number | Tumor cell line name | Compound 2 | Compound 3 | Compound 5 | Compound 6 | Compound 9 | Compound 10 | Compound 11 |
|---|---|---|---|---|---|---|---|---|
| 17 | MFM-223 | 10.32 | 21.85 | 48.27 | 72.16 | 38.29 | 5.63 | 26.49 |
| 18 | MG63 | 15.83 | 27.06 | >100 | >100 | >100 | 4.37 | 77.05 |
| 19 | NCI-H1648 | 8.91 | 13.64 | >100 | >100 | >100 | 6.06 | >100 |
| 20 | NCI-H1703 | 0.063 | 0.15 | 3.43 | 7.16 | 0.33 | 0.021 | 0.89 |
| 21 | NCI-H2170 | 3.46 | 7.89 | >100 | >100 | 84.03 | 1.24 | 72.75 |
| 22 | NCI-H526 | 8.94 | 11.33 | >100 | >100 | >100 | 4.39 | 92.37 |
| 23 | NCI-H661 | 11.35 | 21.08 | >100 | >100 | >100 | 5.47 | >100 |
| 24 | NCI-H716 | 2.84 | 6.09 | 66.69 | 92.13 | 43.06 | 1.93 | 82.17 |
| 25 | SW620 | 4.67 | 10.38 | >100 | >100 | 66.66 | 3.46 | 60.28 |
| 26 | T.T | 8.29 | 19.83 | >100 | >100 | >100 | 4.37 | >100 |
| 27 | TE-15 | 8.45 | 12.74 | >100 | >100 | 88.88 | 6.31 | >100 |
| 28 | TE-6 | 7.03 | 11.28 | >100 | >100 | >100 | 4.11 | >100 |
| 29 | Li-7 | 7.26 | 10.07 | 59.14 | 82.03 | 49.27 | 4.38 | 35.05 |
| 30 | JHH1 | 11.27 | 14.94 | >100 | >100 | >100 | 7.43 | >100 |
| 31 | JHH2 | 36.02 | 40.73 | >100 | >100 | >100 | 25.08 | 93.47 |
| 32 | JHH4 | 5.83 | 12.06 | 60.34 | 79.03 | >100 | 2.31 | 38.68 |
| 33 | JHH5 | 21.34 | 30.97 | >100 | >100 | >100 | 12.38 | 87.65 |
| 34 | JHH6 | 4.38 | 7.51 | 79.26 | >100 | 65.32 | 2.46 | 54.39 |
| 35 | JHH7 | 2.84 | 5.69 | 57.79 | 83.16 | 42.16 | 1.65 | 40.03 |
| 36 | HUH1 | 6.71 | 7.93 | 82.34 | >100 | 52.43 | 3.47 | 50.57 |
| 37 | HUH6 | 0.82 | 1.55 | 72.17 | 88.66 | 50.26 | 0.15 | 46.37 |
| 38 | HUH7 | 4.32 | 6.69 | 77.85 | 92.13 | 30.34 | 2.89 | 42.16 |
| 39 | Hep3B2.1-7 | 3.43 | 5.33 | 76.49 | 95.61 | 52.81 | 1.23 | 50.43 |
| 40 | HEPG2 | 0.64 | 1.73 | 30.79 | 43.35 | 10.96 | 0.37 | 11.14 |
| 41 | HLE | 2.69 | 4.72 | 53.42 | 68.88 | 53.27 | 1.26 | 55.21 |
| 42 | HLF | 4.94 | 7.73 | 63.92 | 82.11 | 63.36 | 3.87 | 49.35 |
| 43 | Alexandercells | 5.21 | 12.67 | >100 | >100 | >100 | 5.31 | 79.46 |
| 44 | SK-HEP-1 | 9.25 | 15.82 | 85.08 | >100 | >100 | 2.75 | 55.39 |
| 45 | SNU182 | 32.07 | 54.16 | >100 | >100 | >100 | 13.28 | >100 |
| 46 | SNU354 | 7.01 | 16.75 | >100 | >100 | 67.29 | 4.57 | 63.26 |
| 47 | SNU387 | 19.38 | 40.15 | >100 | >100 | >100 | 10.49 | >100 |
| 48 | SNU398 | 6.37 | 17.06 | >100 | >100 | 82.71 | 2.99 | 78.96 |
| 49 | SNU423 | 14.38 | 26.06 | >100 | >100 | >100 | 8.62 | >100 |
| 50 | SNU449 | 8.39 | 14.62 | >100 | >100 | 89.95 | 4.91 | >100 |
| 51 | SNU475 | 6.37 | 9.62 | >100 | >100 | 77.76 | 3.88 | 76.07 |
| 52 | SNU739 | 6.33 | 8.05 | >100 | >100 | >100 | 3.87 | 63.96 |
| 53 | SNU761 | 15.28 | 29.06 | >100 | >100 | >100 | 9.04 | 76.95 |
| 54 | SNU886 | 3.75 | 9.06 | >100 | >100 | >100 | 1.45 | >100 |

Note:
Cell lines 29-54 in Table 2 shows the response of the liver cancer cell line to each compound As can be seen from the results of Tables 1 and 2, the IC50 values of compounds 1, 2, 3, and 10 are close to those of Linifanib in almost all tumor cell lines, and the modification of these four compounds hardly functions to block the activity of Linifanib. The modification of the other 8 compounds (compounds 4, 5, 6, 7, 8, 9, 11 and 12) successfully blocked the activity of Linifanib in inhibiting tumor cell proliferation, and the difference in IC50 values between these 8 compounds and the Linifanib is more than 5 times in most tumor cells. There are 3 strains sensitive to Linifanib, KASUMI-1 (leukemia cells), NCI-H1703 (lung cancer cells) and AN3-CA (endometrial cells), with IC50 values of 0.01, 0.02 and 0.19 μM, respectively. The IC50 values for the precursor Linifanib-C12-AA5 were 0.10, 0.08 and 3.14 μM, respectively, with a difference of 10, 4 and 16.7 times, respectively.

Among the 54 commercial tumor cell lines, 26 were liver cancer cell lines, and nearly half of the liver cancer cell lines (12/26, 46%) were moderately sensitive to Linifanib, IC50<5 μM, and at the same time for most of the liver cancer cell lines (15/26, 58%), the IC50 values of precursor Linifanib-C12-AA5 were more than 8 times different than the IC50 values of Linifanib, and almost all liver cancer cells did not respond to the intermediates, as shown Table 1.

Example 45 In Vitro Stability Study (Plasma/Liver Homogenate/Spleen Homogenate)

The purpose of this example was to investigate the stability of the precursor Linifanib-C12-AA5 (compound 8) and the intermediate Linifanib-C12-Asp (compound 12) in plasma, liver homogenate and spleen homogenate (precursor Linifanib-C12-AA5 metabolizes into the intermediates Linifanib-C12-Asp and Linifanib; the intermediate Linifanib-C12-Asp is further metabolized to form Linifanib), and the metabolites were analyzed quantitatively, and the stability of the incubation system was verified with positive drugs, providing references for compound drug evaluation.

1. Instruments and Materials
    Instrument: AP13000 LC/MS, ABI
    Materials: Male SD rats (200-250 g), Beijing Vital River
    Test samples: positive drugs and their metabolites M1 and M2, Linifanib-C12-AA5 and its metabolites Linifanib-C12-ASP and Linifanib.
2. Stability study of Linifanib-C12-AA5 and Linifanib-C12-Asp
    2.1 Linifanib-C12-AA5 and Linifanib-C12-Asp plasma incubation stability study protocol Test animal
    Type: SD rat; Quantity: 2
    Sex: male; weight: 200-250 g;

Experimental Procedure
1. Animal blood was collected, blood samples were placed in EDTA anticoagulation tubes, centrifuged at 3000 g for 15 min at 4° C., plasma was separated, and 2 blood samples were mixed in equal volumes;
2. Weighed and dissolved a certain amount of Linifanib-C12-AA5/Linifanib-C12-Asp in DMSO:MeOH (2:8), prepared 200 μM mother liquor by purity, and added the compound to the plasma to a final concentration of 2 μg/mL. The organic ratio in the system was not more than 0.5%.
3. Incubated in a 37° C. water bath and set the sampling points to 0, 0.5, 1, 2, 4, 6, and 8 h. At each sampling point, 100 μL of each sample was added to 300 μL of acetonitrile (with internal standard) for precipitation, centrifuged at 12,000 rpm for 5 min, and 200 μL of supernatant was taken for analysis by LC-MS/MS.
4. Configured the standard curve to quantify Linifanib, Linifanib-C12-Asp and residual Linifanib-C12-AA5.

2.2 Linifanib-C12-AA5 and Linifanib-C12-Asp liver/spleen homogenate incubation stability study protocol
Test animal
Type: SD rat; Quantity: 2
Sex: Male; Weight: 200-250 g
Experimental Procedure
1. Biological analysis method: established the biological analysis method of the compound Linifanib-C12-Asp and Linifanib;
2. Rat liver/spleen was taken on the day of the experiment, two pieces were cut and mixed, and homogenized with 4 volumes (1 g: 4 mL) phosphate buffer (pH 7.4), and the temperature was controlled to not exceed 10° C. in the homogenization process; quantitative detection of protein, and controlled liver and spleen protein concentration.
3. Added the drug Linifanib-C12-AA5, Linifanib-C12-Asp to the liver/spleen homogenate to a concentration of 1000 ng/mL, the incubation volume was 1 mL, and controlled the concentration of the organic solvent in the incubation system to not exceed 0.5%.
4. Incubated in a 37° C. water bath and took 100 μL of samples at 0, 0.5, 1, 2, 4, 6, and 8 h, respectively. After pre-processing the samples with a definite method, the LC-MS/MS analysis was carried out.
5. Prepared a standard curve with blank liver/spleen homogenate to quantify Linifanib-C12-Asp and Linifanib.

3. Stability Study Results
3.1 Plasma Stability Test Results
Positive drugs were metabolized in plasma to their metabolites as expected over time, indicating that the plasma system was stable and the subsequent test results were reliable.
The results are shown in Table 3.
As can be seen from Table 3, Linifanib-C12-AA5 was stable in plasma and did not produce the intermediates Linifanib-C12-Asp and Linifanib; the intermediate Linifanib-C12-Asp was stably incubated in plasma, and the level of Linifanib produced was close to zero.

TABLE 3

Experimental results of stability study of precursor and intermediate compounds in rat plasma

| concentration | Intermediate produced by precursor | | Linifanib produced by precursor | | Residual intermediate | | Linifanib produced by intermediate | |
|---|---|---|---|---|---|---|---|---|
| ng/ml | Repeat 1 | Repeat 2 | Repeat 1 | Repeat 2 | Repeat 1 | Repeat 2 | Repeat 1 | Repeat 2 |
| 0 h | 0.961 | 0 | 1.96 | 0 | 1900 | 2180 | 24.2 | 23.7 |
| 0.5 h | 0 | 0 | 0 | 0 | 2100 | 2290 | 24.7 | 24.4 |
| 1 h | 0 | 0 | 0 | 0 | 2180 | 2290 | 23.6 | 24.1 |
| 2 h | 0 | 0 | 0 | 0 | 2160 | 2110 | 22.4 | 20.7 |
| 4 h | 0 | 0 | 0 | 0 | 2210 | 2270 | 24.9 | 24.3 |
| 6 h | 0 | 0 | 0 | 0 | 2070 | 1880 | 22 | 21.9 |
| 8 h | 0 | 0 | 0 | 0 | 1940 | 2060 | 25.1 | 20.8 |

3.2 Liver Homogenate Stability Results
The positive drug was metabolized to its metabolite in the liver homogenate as expected over time, and the liver homogenate system was stable, and the subsequent detection results were reliable.
The results of liver homogenate stability of the precursors and intermediates are shown in Tables 4-5 and FIGS. 1-2.

TABLE 4

The First Stability Experiment of Liver Homogenate

| concentration | Intermediate produced by precursor | | Linifanib produced by precursor | | Residual intermediate | | Linifanib produced by intermediate | |
|---|---|---|---|---|---|---|---|---|
| ng/ml | Repeat 1 | Repeat 2 | Repeat 1 | Repeat 2 | Repeat 1 | Repeat 2 | Repeat 1 | Repeat 2 |
| 0 h | 56.4 | 37.7 | 9.81 | 5.48 | 1130 | 1260 | 24.6 | 21.4 |
| 0.5 h | 124 | 54.9 | 28.7 | 27.8 | 1000 | 970 | 41.6 | 70.0 |
| 1 h | | | | | 1130 | 946 | 61.4 | 101 |

TABLE 4-continued

The First Stability Experiment of Liver Homogenate

| concentration | Intermediate produced by precursor | | Linifanib produced by precursor | | Residual intermediate | | Linifanib produced by intermediate | |
|---|---|---|---|---|---|---|---|---|
| ng/ml | Repeat 1 | Repeat 2 | Repeat 1 | Repeat 2 | Repeat 1 | Repeat 2 | Repeat 1 | Repeat 2 |
| 2 h | 70.0 | 96.4 | 88.2 | 81.8 | 1000 | 602 | 80.1 | 135 |
| 4 h | 60.6 | 47.9 | 119 | 119 | 294 | 456 | 123 | 84.6 |
| 6 h | 52.0 | 63.6 | 197 | 179 | 452 | 226 | 129 | 183 |
| 8 h | 55.9 | 48.0 | 201 | 196 | 461 | 185 | 139 | 190 |

TABLE 5

The Second Stability Experiment of Liver Homogenate

| concentration | Intermediate produced by precursor | | Linifanib produced by precursor | | Residual intermediate | | Linifanib produced by intermediate | |
|---|---|---|---|---|---|---|---|---|
| ng/ml | Repeat 1 | Repeat 2 | Repeat 1 | Repeat 2 | Repeat 1 | Repeat 2 | Repeat 1 | Repeat 2 |
| 0 h | 23.3 | 14.3 | 10.2 | 4.48 | 649 | 634 | 14.2 | 13.4 |
| 0.5 h | 15.4 | 14.8 | 15.2 | 15.5 | 452 | 469 | 32.6 | 29.7 |
| 6 h | 46.7 | 43.8 | 115 | 113 | 309 | 340 | 112 | 108 |

Figure 2:
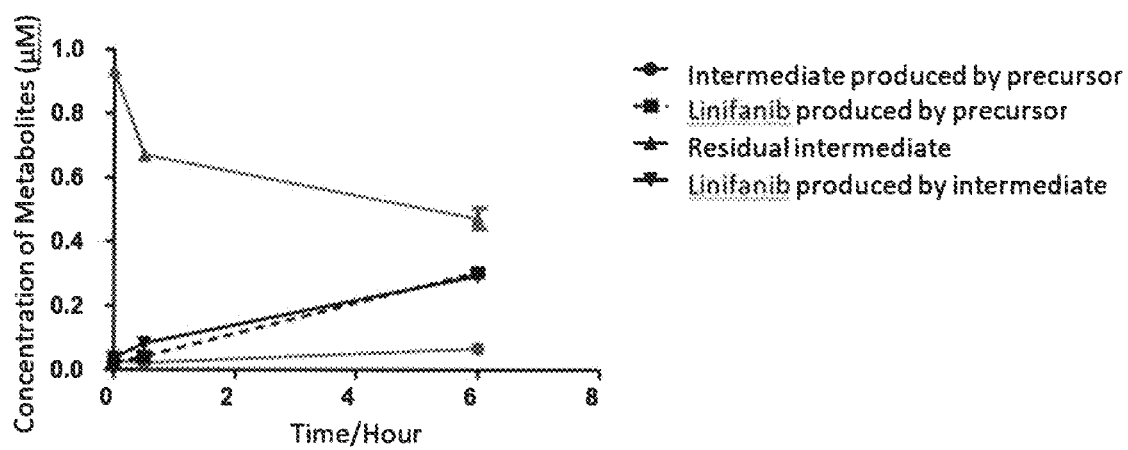
FIG. 2 shows the second experiment of the stability of the precursor and intermediate in liver homogenate

It can be seen from Tables 3-4 and FIGS. 1-2 that the intermediate Linifanib-C12-Asp produced by the precursor Linifanib-C12-AA5 can be rapidly converted into Linifanib in liver homogenate, so the accumulation concentration of intermediates in liver homogenate is relatively low. At the same time, when the same molar concentration of precursors and intermediates were added, the amount of Linifanib formed at each time point in the liver homogenate was basically the same, indicating that the formation of Linifanib was basically generated by the intermediate, direct generation from the precursor was very low.

—3.3 Spleen Homogenization Stability Results

The positive drug was metabolized into its metabolite in the spleen homogenate as expected over time, and the spleen homogenate system was stable, and the subsequent detection results were reliable. The spleen homogenate stability results for the precursors and intermediates are shown in Tables 6-7 and FIGS. 3-4.

TABLE 6

First Stability Experiment of Spleen Homogenate

| concentration | Intermediate produced by precursor | | Linifanib produced by precursor | | Residual intermediate | | Linifanib produced by intermediate | |
|---|---|---|---|---|---|---|---|---|
| ng/ml | Repeat 1 | Repeat 2 | Repeat 1 | Repeat 2 | Repeat 1 | Repeat 2 | Repeat 1 | Repeat 2 |
| 0 h | 53.6 | 47.9 | 2.84 | 2.43 | 900 | 1020 | 36.1 | 19.4 |
| 0.5 h | 329 | 389 | 18.3 | 22.8 | 959 | | 26.7 | |
| 1 h | | 582 | | 55.6 | | | | |
| 2 h | | 618 | | 79.6 | 755 | 681 | 43.7 | 51.1 |
| 4 h | 456 | 547 | 63.0 | 70.3 | 610 | 589 | 50.4 | 58.5 |
| 6 h | 398 | 376 | 68.2 | 60.8 | 470 | 467 | 54.0 | 61.6 |
| 8 h | 454 | 572 | 80.2 | 99.3 | 499 | 506 | 57.0 | 64.2 |

TABLE 7

Second Stability Experiment of Spleen Homogenate

| concentration | Intermediate produced by precursor | | Linifanib produced by precursor | | Residual intermediate | | Linifanib produced by intermediate | |
|---|---|---|---|---|---|---|---|---|
| ng/ml | Repeat 1 | Repeat 2 | Repeat 1 | Repeat 2 | Repeat 1 | Repeat 2 | Repeat 1 | Repeat 2 |
| 0 h | 59.8 | 66 | 8.09 | 6.81 | 812 | 844 | 18.4 | 18.5 |
| 0.5 h | 397 | 445 | 28.9 | 29.2 | 770 | 744 | 29.1 | 27.5 |
| 6 h | 411 | 442 | 108 | 108 | 496 | 483 | 69.7 | 67.3 |

Figure 3:
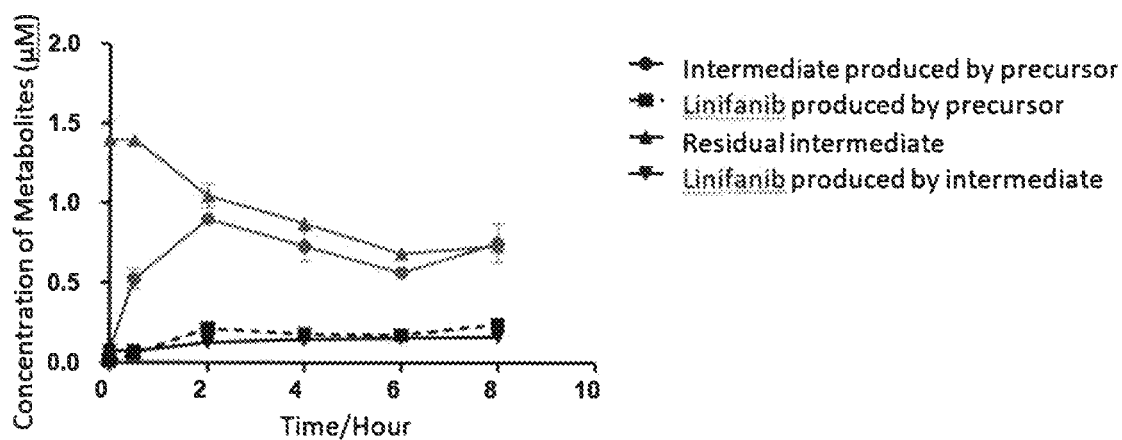
FIG. 3 shows the first experiment of the stability of the precursor and intermediate in spleen homogenate
Figure 4:
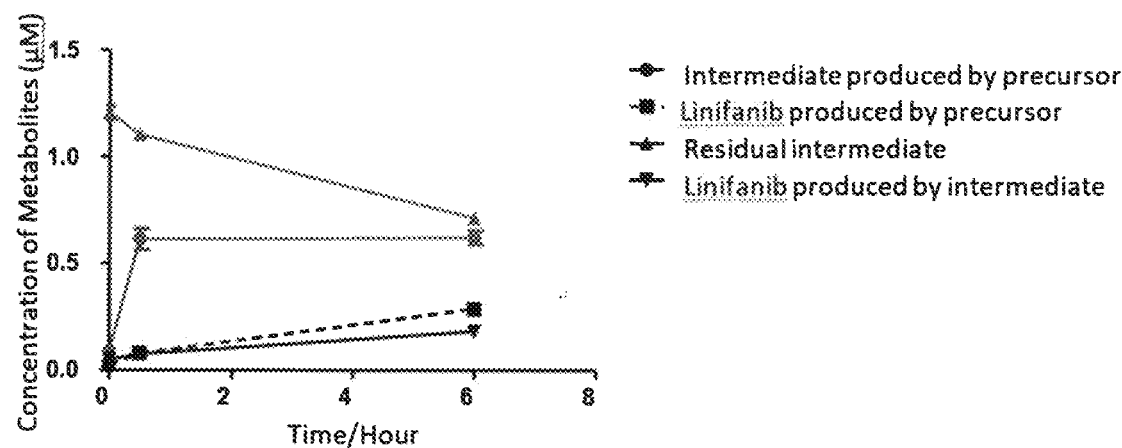
FIG. 4 shows the second experiment of the stability of the precursor and intermediate in spleen homogenate

It can be seen from Tables 6-7 and FIG. 3-4 that the metabolism of the precursor in the spleen homogenate was also the same as in the liver homogenate, and all of them were intermediates, and the intermediate was metabolized to Linifanib.

In addition, the accumulation concentration of the intermediate in the spleen homogenate was higher, and the amount of the produced Linifanib was less than that in the liver homogenate.

From the above results of the in vitro stability study, the following conclusions can be drawn:

(1) The precursor Linifanib-C12-AA5 and the intermediate Linifanib-C12-Asp are stable in plasma.

(2) The metabolic pathway of the precursor Linifanib-C12-AA5 in vitro is basically clear, that is, it is metabolized to the intermediate Linifanib-C12-Asp by PSMA, and then the intermediate Linifanib-C12-Asp is metabolized to the active drug Linifanib by some amide esterase.

Figure 5:
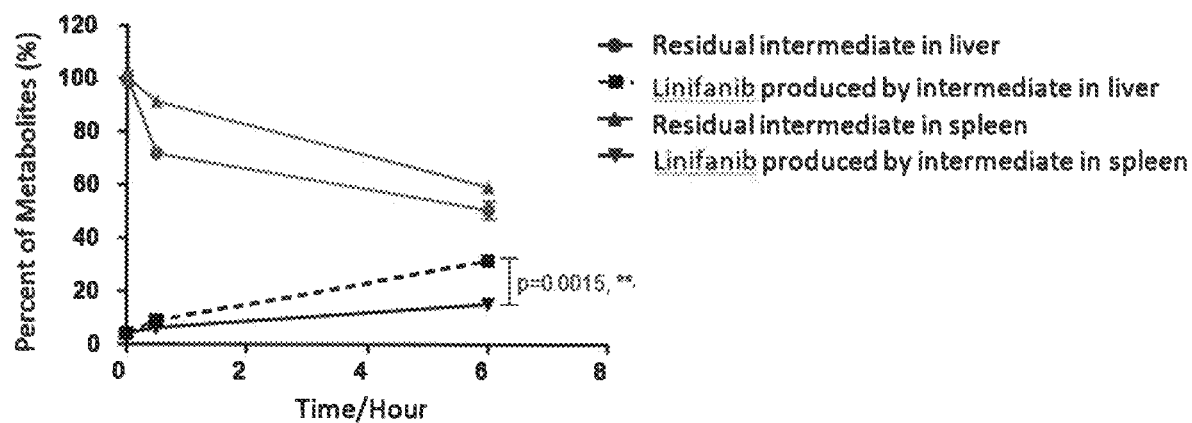
FIG. 5 shows the comparison of liver and spleen homogenate

(3) The active drug Linifanib is produced more in the liver homogenate, as shown in FIG. 5, which shows that the prodrug Linifanib-C12-AA5 is more specifically converted into an active drug in the liver.

The invention claimed is:

1. A pharmaceutical composition comprising a compound of the structure of Formula I, a pharmaceutically acceptable salt, stereoisomer or solvate thereof, and a pharmaceutically acceptable carrier,

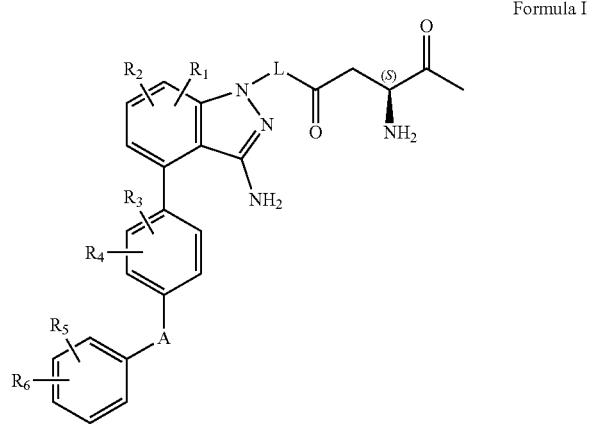

Formula I

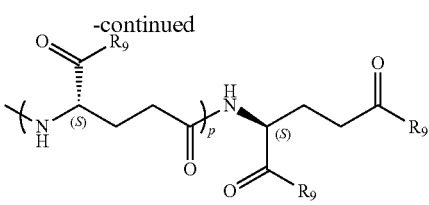

-continued wherein,

A is selected from the groups of (CH2)eN(R7)C(O)N(R8)(CH2)f or CH2C(O)NR7, wherein e and f are independently 0 or 1, wherein the left side of A is the side bonded to the ring substituted by R3 and R4;

L is —[Cm(O)(Z)n(NH)q]-, wherein m, q are 0 or 1, n is 0-11, p is 0-8; Z is —C(R10)$_2$;

R1 and R2 are independently selected from the group consisting of hydrogen, alkoxy, alkoxyalkoxy, alkoxyalkyl, alkyl, aryloxy, aryloxyalkyl, halo, haloalkoxy, haloalkyl, heterocycle, heterocyclylalkenyl, heterocyclylalkoxy, heterocyclylalkyl, heterocyclyloxyalkyl, hydroxy, hydroxyalkoxy, and hydroxyalkyl;

R3 and R4 are independently selected from the group consisting of hydrogen, alkoxy, alkyl, halo, haloalkoxy, haloalkyl and hydroxy;

R5 and R6 are independently selected from the group consisting of hydrogen, alkoxy, alkoxyalkyl, alkoxycarbonyl, alkyl, aryloxy, arylalkyl, carboxy, cyano, halo, haloalkoxy, haloalkyl, Hydroxy, hydroxyalkyl, nitro and —NRcRd;

R7 and R8 are independently selected from the group consisting of hydrogen and alkyl; R9 is selected from the group consisting of hydrogen, hydroxy, amino, alkenyl, alkynyl, alkoxy, alkylamino, alkoxyalkyl, alkyl, alkoxycarbonyl, aryl, heterocycloalkyl;

R10 is selected from the group consisting of hydrogen, alkyl, alkoxy, aryloxy, alkenyloxy, nitro, halo, primary, secondary and tertiary amine;

Ra and Rb are independently selected from the group consisting of hydrogen, alkyl, alkylcarbonyl, alkylsulfonyl, arylsulfonyl, haloalkylsulfonyl and heterocyclylsulfonyl;

Rc and Rd are independently selected from the group consisting of hydrogen, alkyl, alkylcarbonyl, aryl, arylalkyl, cycloalkyl, cycloalkylalkyl, heterocyclyl and heterocyclylalkyl.

2. The pharmaceutical composition according to claim 1, wherein said compound of Formula I is

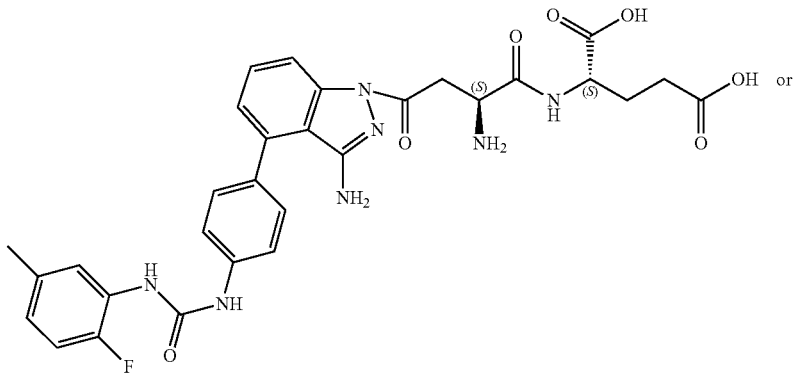

or

-continued
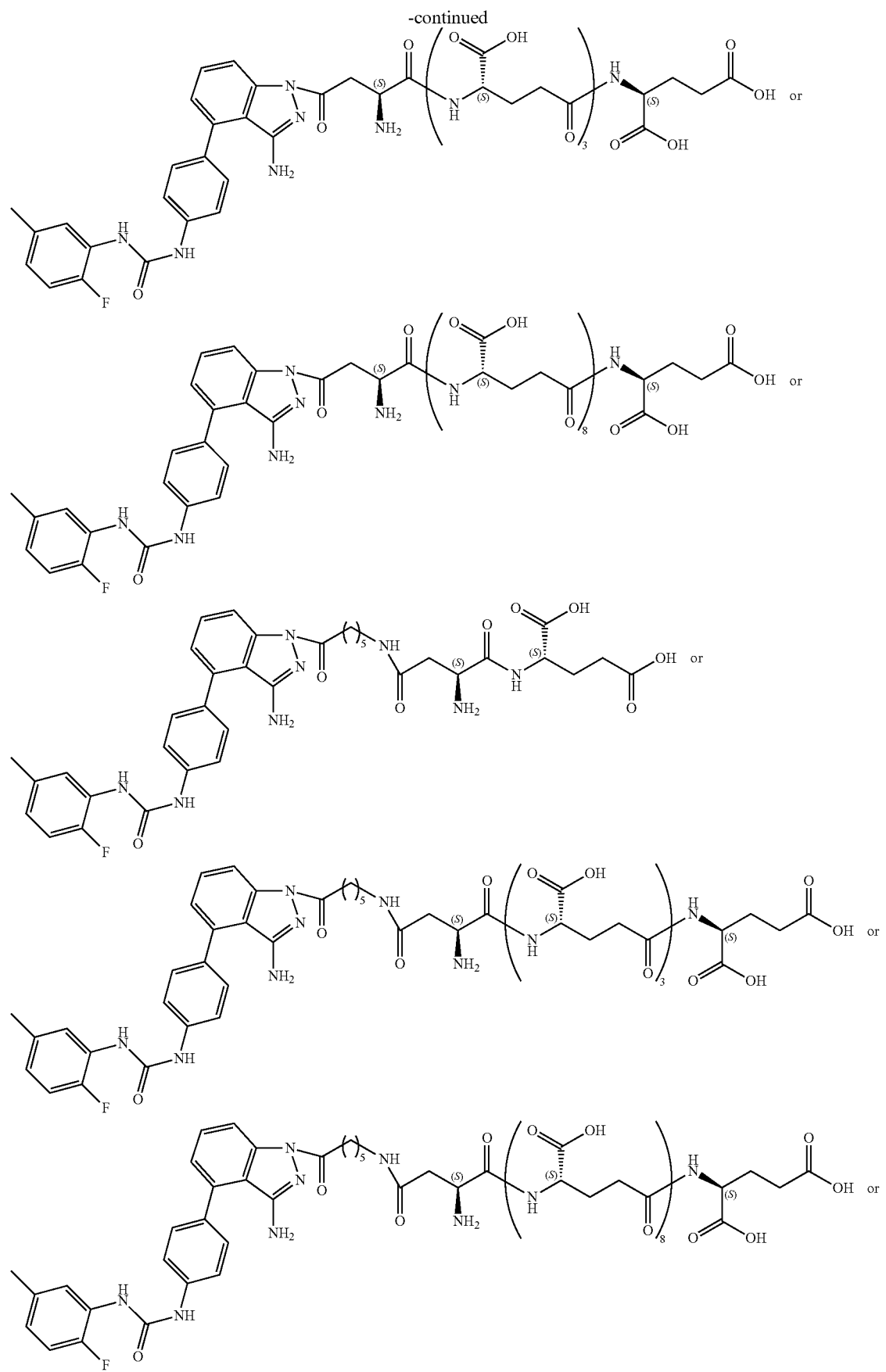

-continued
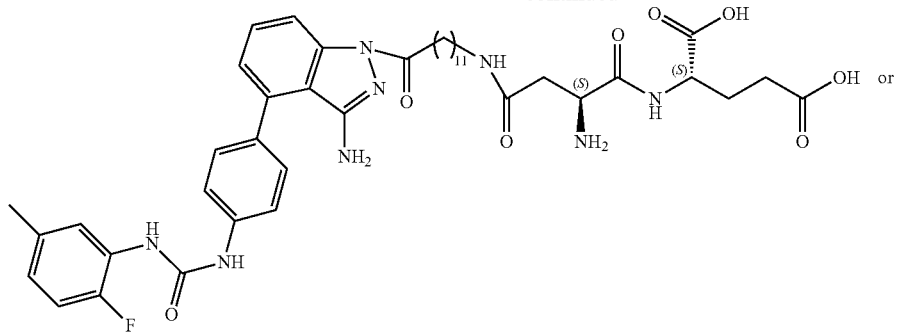
3. A method for preparing a compound of Formula I of claim 1 wherein R9 is hydroxy or a compound of Formula I of claim 2, comprising:
Step (a), Reactant 1, is reacted with Reactant 2, in the presence of a catalyst and a condensing agent to obtain a protecting group-containing intermediate compound 1;
Reactant 1
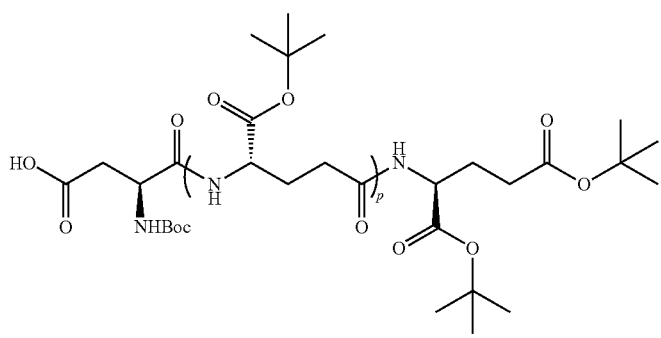

-continued

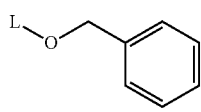
Reactant 2

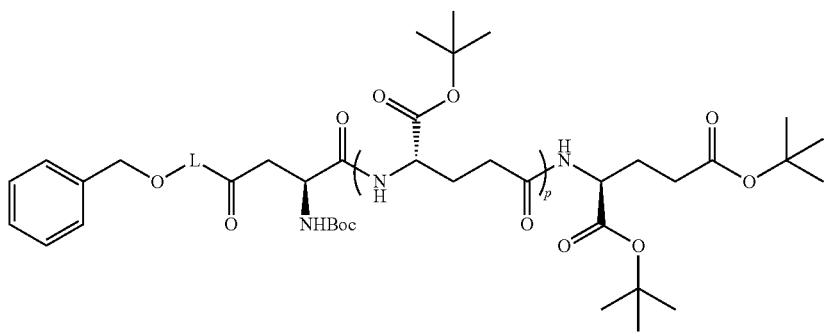
Intermediate compound 1

Step (b), the intermediate compound 1 is subjected to catalytic hydrogenation in a polar solvent to remove the protecting group to obtain an intermediate compound 2;

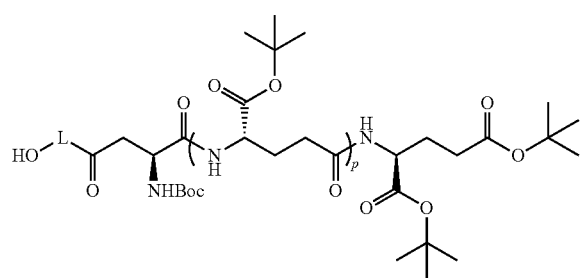
Intermediate compound 2

Step (c), the intermediate compound 2 and Linifanib are reacted in the presence of a catalyst and a condensing agent to obtain an intermediate compound 3;

Step (d), the intermediate compound 3 is subjected to acidic conditions to remove the protecting groups to obtain a compound of Formula I of claim 1 wherein R9 is hydroxy or a compound of Formula I of claim 2.

4. The method according to claim 3, wherein said step (a) is carried out at a reaction temperature of −20° C. to 125° C.; said catalyst is 1-hydroxybenzotriazole; said condensing agent is any one or more agents selected from 1-ethyl-3-(3-dimethylaminopropyl)carbodiimide hydrochloride, 1, 3-dicyclohexylcarbodiimide or 4-dimethylaminopyridine.

5. The method according to claim 3, wherein said step (b) is carried out at a reaction temperature of −20° C. to 125° C.; said catalyst is palladium on carbon or palladium hydroxide, dry or wet.

6. The method according to claim 3, wherein said step (c) is carried out at a reaction temperature of −20° C. to 125° C.; said catalyst is 1-hydroxybenzotriazole; and said condensing agent is any one or more agents selected from ethyl-3-(3-dimethylaminopropyl)carbodiimide hydrochloride, 1, 3-dicyclohexylcarbodiimide or 4-dimethylaminopyridine.

Intermediate compound 3

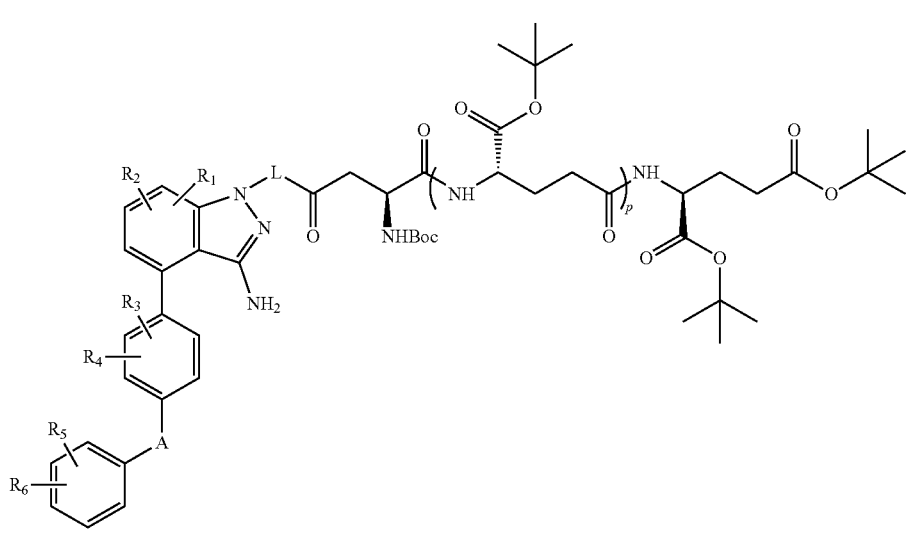

7. The method according to claim 3, wherein said step (d) is carried out at a reaction temperature of −20° C. to 125° C.; and said acidic conditions is formic acid, acetic acid, or trifluoroacetic acid.

8. A method for treating a cancer in a subject, said method comprising:
   administering to a subject in need thereof the pharmaceutical composition according to claim 1 or 2; wherein said cancer is at least one selected from the group of: endometrial cancer, leukemia, colon cancer, breast cancer, liver cancer, lung cancer, prostate cancer, and renal cancer.

9. A method for treating liver cancer in a subject, said method comprising: administering to the subject in need thereof the pharmaceutical composition according to claim 1 or 2.

* * * * *